US009678089B2

(12) United States Patent
Montgomery

(10) Patent No.: US 9,678,089 B2
(45) Date of Patent: Jun. 13, 2017

(54) METHODS AND KITS FOR MEASURING VON WILLEBRAND FACTOR

(71) Applicants: BloodCenter Research Foundation, Milwaukee, WI (US); The Medical College of Wisconsin, Inc., Milwaukee, WI (US)

(72) Inventor: Robert Montgomery, Cedarburg, WI (US)

(73) Assignees: BLOOD CENTER RESEARCH FOUNDATION, Milwaukee, WI (US); THE MEDICAL COLLEGE OF WISCONSIN, INC., Milwaukee, WI (US)

( * ) Notice: Subject to any disclaimer, the term of this patent is extended or adjusted under 35 U.S.C. 154(b) by 28 days.

(21) Appl. No.: 14/485,926

(22) Filed: Sep. 15, 2014

(65) Prior Publication Data

US 2015/0185214 A1 Jul. 2, 2015

Related U.S. Application Data

(63) Continuation of application No. 13/669,866, filed on Nov. 6, 2012, now Pat. No. 8,865,415, which is a continuation of application No. 13/153,105, filed on Jun. 3, 2011, now Pat. No. 8,318,444, which is a continuation of application No. 12/197,057, filed on Aug. 22, 2008, now Pat. No. 8,163,496.

(60) Provisional application No. 60/957,604, filed on Aug. 23, 2007.

(51) Int. Cl.

*G01N 33/86* (2006.01)
*C07K 14/745* (2006.01)
*G01N 33/50* (2006.01)
*G01N 33/554* (2006.01)

(52) U.S. Cl.

CPC ........... *G01N 33/86* (2013.01); *C07K 14/745* (2013.01); *G01N 33/5008* (2013.01); *G01N 33/554* (2013.01); *G01N 2333/47* (2013.01); *G01N 2333/705* (2013.01); *G01N 2333/755* (2013.01); *G01N 2800/224* (2013.01)

(58) Field of Classification Search

None

See application file for complete search history.

(56) References Cited

U.S. PATENT DOCUMENTS

| | | | | |
|---|---|---|---|---|
| 8,163,496 | B2 | 4/2012 | Montgomery | |
| 8,318,444 | B2 | 11/2012 | Montgomery | |
| 8,865,415 | B2 * | 10/2014 | Montgomery ..... | G01N 33/5008 435/7.1 |
| 2010/0136589 | A1 | 6/2010 | Althaus et al. | |

FOREIGN PATENT DOCUMENTS

| | | | |
|---|---|---|---|
| WO | 0102853 | A2 | 1/2001 |
| WO | 2009007051 | A3 | 1/2009 |

OTHER PUBLICATIONS

Biswas et al., Properties of Soluble His-Tagged rGPIbal-483 Wild-Type and Increase-of-Function Mutants; USA, Blood (ASH annual meeting abstracts) 2005, 106 Abstract 3949.

Dong, et al., Novel Gain-of-function Mutations of Platelet Glycoprotein Ibalpha by Valine Mutagenesis in the Cys209-Cys248 Disulfide Loop, Journal of Biological Chemistry, 2000, 275(36):27663-27670.

Enayat et al., Thromb Haemost. Nov. 2012: 108(5):946-54. doi: 10.1160/TH12-04-0189. Epub Sep. 26, 2012.

Federici, et al., A Sensitive Ristocetin Co-Factor Activity Assay with Recombinant Glycoprotein Ibalpha for the Diagnosis of Patients with Low von Willebrand Factor Levels, Haematologica, 2004, 89(1 ):77-85.

Hickey, et al., Characterization of the Gene Encoding Human Platelet Glycoprotein IX, Journal of Biological Chemistry, 1993, 268(5):3438-3443.

Tait, et aL, Phenotype Oranges Resulting in High-Affinity Binding of von Wiilebrand Factor to Recombinant Glycoprotein Ib-IX: Analysis of the Platelet-Type von Willebrand Disease Mutations, Blood, 2001, 98(6): 1812-1818.

Ulrichts, et al., Von Willebrand Factor But Not alpha-Thrombin Binding to Platelet Glycoprotein Ibalpha Is Influenced by the HPA-2 Polymorphism, Arterioscler Thromb Vase Bioi, 2003, 23:1302-1307.

Yagi, et al., Structural Characterization and Chromosomal Location of the Gene Encoding Human Platelet Glycoprotein Ibbeta, Journal of Biological Chemistry, 1994, 269(26):17424-17427.

PCT International Search Report and Written Opinion, PCT/US08/74083, Dec. 4, 2008.

European Patent Office, Examination Report, EP 08798536.2, Mar. 25, 2011.

Applicant, response to Mar. 25, 2011 Examination report, EP 08798536.2, Sep. 29, 2011.

U.S. Appl. No. 12/197,057, Non-Final Office Action mailed Sep. 27, 2010.

Applicant, Response to Non-Final Office Action mailed Sep. 27, 2010, U.S. Appl. No. 12/197,057.

U.S. Appl. No. 12/197,057, Final Office Action mailed Mar. 25, 2011.

Applicant, response to Final Office Action mailed Mar. 25, 2011 Accompanying request for Continued Examination, U.S. Appl. No. 12/197,057.

* cited by examiner

*Primary Examiner* — Michael Szperka

(74) *Attorney, Agent, or Firm* — Quarles & Brady LLP

(57) ABSTRACT

Methods and kits for measuring levels of von Willebrand factor function in a sample without using a platelet aggregation agonist, such as ristocetin, comprising recombinant glycoprotein Ibα having a combination of G233V, D235Y and M239V mutations and an agent to detect a complex between the recombinant glycoprotein Ibα and von Willebrand factor.

16 Claims, 8 Drawing Sheets

SEQUENCE LISTING

```
<160> NUMBER OF SEQ ID NOS: 9

<210> SEQ ID NO 1
<211> LENGTH: 2463
<212> TYPE: DNA
<213> ORGANISM: Homo sapiens
<220> FEATURE:
<221> NAME/KEY: CDS
<222> LOCATION: (76)..(1992)
<220> FEATURE:
<221> NAME/KEY: sig_peptide
<222> LOCATION: (76)..(123)
<220> FEATURE:
```

```
<221> NAME/KEY: mat_peptide
<222> LOCATION: (124)..(1992)

<400> SEQUENCE: 1

gagagaagga cggagtcgag tggcacccta gaagacgctc tgtgccttcg gaggtctttc      60

tgcctgcctg tcctc atg cct ctc ctc ctc ttg ctg ctc ctg ctg cca agc      111
                 Met Pro Leu Leu Leu Leu Leu Leu Leu Leu Pro Ser
                     -15                 -10                 -5

ccc tta cac ccc cac ccc atc tgt gag gtc tcc aaa gtg gcc agc cac      159
Pro Leu His Pro His Pro Ile Cys Glu Val Ser Lys Val Ala Ser His
            -1  1               5                   10

cta gaa gtg aac tgt gac aag agg aat ctg aca gcg ctg cct cca gac      207
Leu Glu Val Asn Cys Asp Lys Arg Asn Leu Thr Ala Leu Pro Pro Asp
        15                  20                  25

ctg ccg aaa gac aca acc atc ctc cac ctg agt gag aac ctc ctg tac      255
Leu Pro Lys Asp Thr Thr Ile Leu His Leu Ser Glu Asn Leu Leu Tyr
    30                  35                  40

acc ttc tcc ctg gca acc ctg atg cct tac act cgc ctc act cag ctg      303
Thr Phe Ser Leu Ala Thr Leu Met Pro Tyr Thr Arg Leu Thr Gln Leu
45                  50                  55                  60

aac cta gat agg tgc gag ctc acc aag ctc cag gtc gat ggg acg ctg      351
Asn Leu Asp Arg Cys Glu Leu Thr Lys Leu Gln Val Asp Gly Thr Leu
                65                  70                  75

cca gtg ctg ggg acc ctg gat cta tcc cac aat cag ctg caa agc ctg      399
Pro Val Leu Gly Thr Leu Asp Leu Ser His Asn Gln Leu Gln Ser Leu
            80                  85                  90

ccc ttg cta ggg cag aca ctg cct gct ctc acc gtc ctg gac gtc tcc      447
Pro Leu Leu Gly Gln Thr Leu Pro Ala Leu Thr Val Leu Asp Val Ser
        95                  100                 105

ttc aac cgg ctg acc tcg ctg cct ctt ggt gcc ctg cgt ggt ctt ggc      495
Phe Asn Arg Leu Thr Ser Leu Pro Leu Gly Ala Leu Arg Gly Leu Gly
    110                 115                 120

gaa ctc caa gag ctc tac ctg aaa ggc aat gag ctg aag acc ctg ccc      543
Glu Leu Gln Glu Leu Tyr Leu Lys Gly Asn Glu Leu Lys Thr Leu Pro
125                 130                 135                 140

cca ggg ctc ctg acg ccc aca ccc aag ctg gag aag ctc agt ctg gct      591
Pro Gly Leu Leu Thr Pro Thr Pro Lys Leu Glu Lys Leu Ser Leu Ala
                145                 150                 155

aac aac aac ttg act gag ctc ccc gct ggg ctc ctg aat ggg ctg gag      639
Asn Asn Asn Leu Thr Glu Leu Pro Ala Gly Leu Leu Asn Gly Leu Glu
            160                 165                 170

aat ctc gac acc ctt ctc ctc caa gag aac tcg ctg tat aca ata cca      687
Asn Leu Asp Thr Leu Leu Leu Gln Glu Asn Ser Leu Tyr Thr Ile Pro
        175                 180                 185

aag ggc ttt ttt ggg tcc cac ctc ctg cct ttt gct ttt ctc cac ggg      735
Lys Gly Phe Phe Gly Ser His Leu Leu Pro Phe Ala Phe Leu His Gly
    190                 195                 200

aac ccc tgg tta tgc aac tgt gag atc ctc tat ttt cgt cgc tgg ctg      783
Asn Pro Trp Leu Cys Asn Cys Glu Ile Leu Tyr Phe Arg Arg Trp Leu
205                 210                 215                 220

cag gac aat gct gaa aat gtc tac gta tgg aag caa ggt gtg gac gtc      831
Gln Asp Asn Ala Glu Asn Val Tyr Val Trp Lys Gln Gly Val Asp Val
                225                 230                 235

aag gcc atg acc tct aat gtg gcc agt gtg cag tgt gac aat tca gac      879
Lys Ala Met Thr Ser Asn Val Ala Ser Val Gln Cys Asp Asn Ser Asp
            240                 245                 250

aag ttt ccc gtc tac aaa tac cca gga aag ggg tgc ccc acc ctt ggt      927
Lys Phe Pro Val Tyr Lys Tyr Pro Gly Lys Gly Cys Pro Thr Leu Gly
        255                 260                 265
```

-continued

```
gat gaa ggt gac aca gac cta tat gat tac tac cca gaa gag gac act      975
Asp Glu Gly Asp Thr Asp Leu Tyr Asp Tyr Tyr Pro Glu Glu Asp Thr
    270                 275                 280

gag ggc gat aag gtg cgt gcc aca agg act gtg gtc aag ttc ccc acc     1023
Glu Gly Asp Lys Val Arg Ala Thr Arg Thr Val Val Lys Phe Pro Thr
285                 290                 295                 300

aaa gcc cat aca acc ccc tgg ggt cta ttc tac tca tgg tcc act gct     1071
Lys Ala His Thr Thr Pro Trp Gly Leu Phe Tyr Ser Trp Ser Thr Ala
                305                 310                 315

tct cta gac agc caa atg ccc tcc tcc ttg cat cca aca caa gaa tcc     1119
Ser Leu Asp Ser Gln Met Pro Ser Ser Leu His Pro Thr Gln Glu Ser
            320                 325                 330

act aag gag cag acc aca ttc cca cct aga tgg acc cca aat ttc aca     1167
Thr Lys Glu Gln Thr Thr Phe Pro Pro Arg Trp Thr Pro Asn Phe Thr
        335                 340                 345

ctt cac atg gaa tcc atc aca ttc tcc aaa act cca aaa tcc act act     1215
Leu His Met Glu Ser Ile Thr Phe Ser Lys Thr Pro Lys Ser Thr Thr
    350                 355                 360

gaa cca acc cca agc ccg acc acc tca gag ccc gtc ccg gag ccc gcc     1263
Glu Pro Thr Pro Ser Pro Thr Thr Ser Glu Pro Val Pro Glu Pro Ala
365                 370                 375                 380

cca aac atg acc acc ctg gag ccc act cca agc ccg acc acc cca gag     1311
Pro Asn Met Thr Thr Leu Glu Pro Thr Pro Ser Pro Thr Thr Pro Glu
                385                 390                 395

ccc acc tca gag ccc gcc ccc agc ccg acc acc ccg gag ccc acc tca     1359
Pro Thr Ser Glu Pro Ala Pro Ser Pro Thr Thr Pro Glu Pro Thr Ser
            400                 405                 410

gag ccc gcc ccc agc ccg acc acc ccg gag ccc acc cca atc ccg acc     1407
Glu Pro Ala Pro Ser Pro Thr Thr Pro Glu Pro Thr Pro Ile Pro Thr
        415                 420                 425

atc gcc aca agc ccg acc atc ctg gtg tct gcc aca agc ctg atc act     1455
Ile Ala Thr Ser Pro Thr Ile Leu Val Ser Ala Thr Ser Leu Ile Thr
    430                 435                 440

cca aaa agc aca ttt tta act acc aca aaa ccc gta tca ctc tta gaa     1503
Pro Lys Ser Thr Phe Leu Thr Thr Thr Lys Pro Val Ser Leu Leu Glu
445                 450                 455                 460

tcc acc aaa aaa acc atc cct gaa ctt gat cag cca cca aag ctc cgt     1551
Ser Thr Lys Lys Thr Ile Pro Glu Leu Asp Gln Pro Pro Lys Leu Arg
                465                 470                 475

ggg gtg ctc caa ggg cat ttg gag agc tcc aga aat gac cct ttt ctc     1599
Gly Val Leu Gln Gly His Leu Glu Ser Ser Arg Asn Asp Pro Phe Leu
            480                 485                 490

cac ccc gac ttt tgc tgc ctc ctc ccc ctg ggc ttc tat gtc ttg ggt     1647
His Pro Asp Phe Cys Cys Leu Leu Pro Leu Gly Phe Tyr Val Leu Gly
        495                 500                 505

ctc ttc tgg ctg ctc ttt gcc tct gtg gtc ctc atc ctg ctg ctg agc     1695
Leu Phe Trp Leu Leu Phe Ala Ser Val Val Leu Ile Leu Leu Leu Ser
    510                 515                 520

tgg gtt ggg cat gtg aaa cca cag gcc ctg gac tct ggc caa ggt gct     1743
Trp Val Gly His Val Lys Pro Gln Ala Leu Asp Ser Gly Gln Gly Ala
525                 530                 535                 540

gct ctg acc aca gcc aca caa acc aca cac ctg gag ctg cag agg gga     1791
Ala Leu Thr Thr Ala Thr Gln Thr Thr His Leu Glu Leu Gln Arg Gly
                545                 550                 555

cgg caa gtg aca gtg ccc cgg gcc tgg ctg ctc ttc ctt cga ggt tcg     1839
Arg Gln Val Thr Val Pro Arg Ala Trp Leu Leu Phe Leu Arg Gly Ser
            560                 565                 570

ctt ccc act ttc cgc tcc agc ctc ttc ctg tgg gta cgg cct aat ggc     1887
Leu Pro Thr Phe Arg Ser Ser Leu Phe Leu Trp Val Arg Pro Asn Gly
        575                 580                 585
```

```
cgt gtg ggg cct cta gtg gca gga agg agg ccc tca gct ctg agt cag     1935
Arg Val Gly Pro Leu Val Ala Gly Arg Arg Pro Ser Ala Leu Ser Gln
    590                 595                 600

ggt cgt ggt cag gac ctg ctg agc aca gtg agc att agg tac tct ggc     1983
Gly Arg Gly Gln Asp Leu Leu Ser Thr Val Ser Ile Arg Tyr Ser Gly
605                 610                 615                 620

cac agc ctc tgagggtggg aggtttgggg accttgagag aagagcctgt             2032
His Ser Leu

gggctctcct attggaatct agttgggggt tggaggggta aggaacacag ggtgataggg   2092

gaggggtctt agttcctttt tctgtatcag aagccctgtc ttcacaacac aggcacacaa   2152

tttcagtccc agccaaagca gaaggggtaa tgacatggac ttggcggggg gacaagacaa   2212

agctcccgat gctgcatggg gcgctgccag atctcacggt gaaccatttt ggcagaatac   2272

agcatggttc ccacatgcat ctatgcacag aagaaaatct ggaaagtgat ttatcaggat   2332

gtgagcactc gttgtgtctg gatgttacaa atatgggtgg ttttattttc tttttccctg   2392

tttagcattt tctagttttc cactattatt gtatattatc tgtataataa aaaataattt   2452

tagggttggg a                                                        2463


<210> SEQ ID NO 2
<211> LENGTH: 639
<212> TYPE: PRT
<213> ORGANISM: Homo sapiens

<400> SEQUENCE: 2

Met Pro Leu Leu Leu Leu Leu Leu Leu Leu Pro Ser Pro Leu His Pro
    -15                 -10                 -5                  -1

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
```

```
    210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Ala Thr Arg Thr Val Val Lys Phe Pro Thr Lys Ala His Thr
    290                 295                 300

Thr Pro Trp Gly Leu Phe Tyr Ser Trp Ser Thr Ala Ser Leu Asp Ser
305                 310                 315                 320

Gln Met Pro Ser Ser Leu His Pro Thr Gln Glu Ser Thr Lys Glu Gln
                325                 330                 335

Thr Thr Phe Pro Pro Arg Trp Thr Pro Asn Phe Thr Leu His Met Glu
            340                 345                 350

Ser Ile Thr Phe Ser Lys Thr Pro Lys Ser Thr Thr Glu Pro Thr Pro
        355                 360                 365

Ser Pro Thr Thr Ser Glu Pro Val Pro Glu Pro Ala Pro Asn Met Thr
    370                 375                 380

Thr Leu Glu Pro Thr Pro Ser Pro Thr Thr Pro Glu Pro Thr Ser Glu
385                 390                 395                 400

Pro Ala Pro Ser Pro Thr Thr Pro Glu Pro Thr Ser Glu Pro Ala Pro
                405                 410                 415

Ser Pro Thr Thr Pro Glu Pro Thr Pro Ile Pro Thr Ile Ala Thr Ser
            420                 425                 430

Pro Thr Ile Leu Val Ser Ala Thr Ser Leu Ile Thr Pro Lys Ser Thr
        435                 440                 445

Phe Leu Thr Thr Thr Lys Pro Val Ser Leu Leu Glu Ser Thr Lys Lys
    450                 455                 460

Thr Ile Pro Glu Leu Asp Gln Pro Pro Lys Leu Arg Gly Val Leu Gln
465                 470                 475                 480

Gly His Leu Glu Ser Ser Arg Asn Asp Pro Phe Leu His Pro Asp Phe
                485                 490                 495

Cys Cys Leu Leu Pro Leu Gly Phe Tyr Val Leu Gly Leu Phe Trp Leu
            500                 505                 510

Leu Phe Ala Ser Val Val Leu Ile Leu Leu Leu Ser Trp Val Gly His
        515                 520                 525

Val Lys Pro Gln Ala Leu Asp Ser Gly Gln Gly Ala Ala Leu Thr Thr
    530                 535                 540

Ala Thr Gln Thr Thr His Leu Glu Leu Gln Arg Gly Arg Gln Val Thr
545                 550                 555                 560

Val Pro Arg Ala Trp Leu Leu Phe Leu Arg Gly Ser Leu Pro Thr Phe
                565                 570                 575

Arg Ser Ser Leu Phe Leu Trp Val Arg Pro Asn Gly Arg Val Gly Pro
            580                 585                 590

Leu Val Ala Gly Arg Arg Pro Ser Ala Leu Ser Gln Gly Arg Gly Gln
        595                 600                 605

Asp Leu Leu Ser Thr Val Ser Ile Arg Tyr Ser Gly His Ser Leu
    610                 615                 620
```

<210> SEQ ID NO 3

```
<211> LENGTH: 958
<212> TYPE: DNA
<213> ORGANISM: Homo sapiens
<220> FEATURE:
<221> NAME/KEY: CDS
<222> LOCATION: (28)..(645)

<400> SEQUENCE: 3

agtaagccgg gctgccgtct tctcgcc atg ggc tcc ggg ccg cgc ggg gcg ctg      54
                              Met Gly Ser Gly Pro Arg Gly Ala Leu
                              1               5

agc tta ctg ctc ctg ctg ctg gcc ccg ccg agc cgc ccg gcc gca ggt       102
Ser Leu Leu Leu Leu Leu Leu Ala Pro Pro Ser Arg Pro Ala Ala Gly
10                  15                  20                  25

tgc ccg gcg ccc tgt agc tgc gcg ggg acg ctc gtg gac tgc ggg cgc       150
Cys Pro Ala Pro Cys Ser Cys Ala Gly Thr Leu Val Asp Cys Gly Arg
                30                  35                  40

cgc ggg ctg act tgg gcc tcg ctg ccg acc gcc ttc cct gtc gac aca       198
Arg Gly Leu Thr Trp Ala Ser Leu Pro Thr Ala Phe Pro Val Asp Thr
            45                  50                  55

acc gag ctg gtg ctg acc ggc aac aac ctg acg gcg ctg ccg ccg ggg       246
Thr Glu Leu Val Leu Thr Gly Asn Asn Leu Thr Ala Leu Pro Pro Gly
        60                  65                  70

ctg ctg gac gcg ctg ccc gcg ctg cgc acc gca cac ctg ggc gcc aac       294
Leu Leu Asp Ala Leu Pro Ala Leu Arg Thr Ala His Leu Gly Ala Asn
    75                  80                  85

ccc tgg cgc tgc gac tgc cgc ctt gtg ccg ctg cgc gcc tgg ctg gcc       342
Pro Trp Arg Cys Asp Cys Arg Leu Val Pro Leu Arg Ala Trp Leu Ala
90                  95                  100                 105

ggc cgc ccc gag cgt gcg ccc tac cgc gac ctg cgt tgc gtg gcg ccc       390
Gly Arg Pro Glu Arg Ala Pro Tyr Arg Asp Leu Arg Cys Val Ala Pro
                110                 115                 120

cca gcg ctg cgc ggc cgc ctg ctg ccc tat ctg gcc gag gac gag ctg       438
Pro Ala Leu Arg Gly Arg Leu Leu Pro Tyr Leu Ala Glu Asp Glu Leu
            125                 130                 135

cgc gcc gct tgc gct ccc ggc ccg ctc tgc tgg ggg gcg ctg gcg gcg       486
Arg Ala Ala Cys Ala Pro Gly Pro Leu Cys Trp Gly Ala Leu Ala Ala
        140                 145                 150

cag ctt gcg ctg ctg ggc ctt ggg ctg ctg cac gcg ttg ctg ctg gtg       534
Gln Leu Ala Leu Leu Gly Leu Gly Leu Leu His Ala Leu Leu Leu Val
    155                 160                 165

ctg ctg ctg tgc cgc ctg cgg agg ctg cgg gcc cgg gcc cgc gct cgc       582
Leu Leu Leu Cys Arg Leu Arg Arg Leu Arg Ala Arg Ala Arg Ala Arg
170                 175                 180                 185

gcc gca gcc cgg ctg tcg ctg acc gac ccg ctg gtg gcc gag cga gcc       630
Ala Ala Ala Arg Leu Ser Leu Thr Asp Pro Leu Val Ala Glu Arg Ala
                190                 195                 200

gga acc gac gag tcc tgaggagaga accggtgcgt cctgaggaga gaaccggcgc       685
Gly Thr Asp Glu Ser
            205

tgggcaacac gggcctgcaa actcgacagg accctgcccg aggggccctc gcgccaacct     745

ggaccggtcc ccgcctcctc cgctgcccaa tctctcagac ccaccccacc tgcaggccca     805

gaccacgtgg gacagaactc ctgcccaccc taccccgagg gaggcgaacc cgcacttcca     865

ggcttgggag gaccatgggg cacaatgcgg tccagaccct gctgcgtctc ccttccaaac     925

tctggtgctg aataaaccct tctgatctgg tct                                  958


<210> SEQ ID NO 4
<211> LENGTH: 206
<212> TYPE: PRT
```

```
<213> ORGANISM: Homo sapiens

<400> SEQUENCE: 4

Met Gly Ser Gly Pro Arg Gly Ala Leu Ser Leu Leu Leu Leu Leu Leu
1               5                   10                  15

Ala Pro Pro Ser Arg Pro Ala Ala Gly Cys Pro Ala Pro Cys Ser Cys
            20                  25                  30

Ala Gly Thr Leu Val Asp Cys Gly Arg Arg Gly Leu Thr Trp Ala Ser
        35                  40                  45

Leu Pro Thr Ala Phe Pro Val Asp Thr Thr Glu Leu Val Leu Thr Gly
    50                  55                  60

Asn Asn Leu Thr Ala Leu Pro Pro Gly Leu Leu Asp Ala Leu Pro Ala
65                  70                  75                  80

Leu Arg Thr Ala His Leu Gly Ala Asn Pro Trp Arg Cys Asp Cys Arg
                85                  90                  95

Leu Val Pro Leu Arg Ala Trp Leu Ala Gly Arg Pro Glu Arg Ala Pro
            100                 105                 110

Tyr Arg Asp Leu Arg Cys Val Ala Pro Pro Ala Leu Arg Gly Arg Leu
        115                 120                 125

Leu Pro Tyr Leu Ala Glu Asp Glu Leu Arg Ala Ala Cys Ala Pro Gly
    130                 135                 140

Pro Leu Cys Trp Gly Ala Leu Ala Ala Gln Leu Ala Leu Leu Gly Leu
145                 150                 155                 160

Gly Leu Leu His Ala Leu Leu Leu Val Leu Leu Leu Cys Arg Leu Arg
                165                 170                 175

Arg Leu Arg Ala Arg Ala Arg Ala Arg Ala Ala Ala Arg Leu Ser Leu
            180                 185                 190

Thr Asp Pro Leu Val Ala Glu Arg Ala Gly Thr Asp Glu Ser
        195                 200                 205


<210> SEQ ID NO 5
<211> LENGTH: 3493
<212> TYPE: DNA
<213> ORGANISM: Homo sapiens
<220> FEATURE:
<221> NAME/KEY: CDS
<222> LOCATION: (32)..(1711)

<400> SEQUENCE: 5

agttactttg gagtgcagaa ccatttcaga c atg ctg agg ggg act cta ctg        52
                                   Met Leu Arg Gly Thr Leu Leu
                                   1               5

tgc gcg gtg ctc ggg ctt ctg cgc gcc cag ccc ttc ccc tgt ccg cca      100
Cys Ala Val Leu Gly Leu Leu Arg Ala Gln Pro Phe Pro Cys Pro Pro
        10                  15                  20

gct tgc aag tgt gtc ttc cgg gac gcc gcg cag tgc tcg ggg ggc gac      148
Ala Cys Lys Cys Val Phe Arg Asp Ala Ala Gln Cys Ser Gly Gly Asp
    25                  30                  35

gtg gcg cgc atc tcc gcg cta ggc ctg ccc acc aac ctc acg cac atc      196
Val Ala Arg Ile Ser Ala Leu Gly Leu Pro Thr Asn Leu Thr His Ile
40                  45                  50                  55

ctg ctc ttc gga atg ggc cgc ggc gtc ctg cag agc cag agc ttc agc      244
Leu Leu Phe Gly Met Gly Arg Gly Val Leu Gln Ser Gln Ser Phe Ser
                60                  65                  70

ggc atg acc gtc ctg cag cgc ctc atg atc tcc gac agc cac att tcc      292
Gly Met Thr Val Leu Gln Arg Leu Met Ile Ser Asp Ser His Ile Ser
            75                  80                  85

gcc gtt gcc ccc ggc acc ttc agt gac ctg ata aaa ctg aaa acc ctg      340
```

-continued

```
Ala Val Ala Pro Gly Thr Phe Ser Asp Leu Ile Lys Leu Lys Thr Leu
        90                  95                  100

agg ctg tcg cgc aac aaa atc acg cat ctt cca ggt gcg ctg ctg gat      388
Arg Leu Ser Arg Asn Lys Ile Thr His Leu Pro Gly Ala Leu Leu Asp
    105                 110                 115

aag atg gtg ctc ctg gag cag ttg ttt ttg gac cac aat gcg cta agg      436
Lys Met Val Leu Leu Glu Gln Leu Phe Leu Asp His Asn Ala Leu Arg
120                 125                 130                 135

ggc att gac caa aac atg ttt cag aaa ctg gtt aac ctg cag gag ctc      484
Gly Ile Asp Gln Asn Met Phe Gln Lys Leu Val Asn Leu Gln Glu Leu
                140                 145                 150

gct ctg aac cag aat cag ctc gat ttc ctt cct gcc agt ctc ttc acg      532
Ala Leu Asn Gln Asn Gln Leu Asp Phe Leu Pro Ala Ser Leu Phe Thr
            155                 160                 165

aat ctg gag aac ctg aag ttg ttg gat tta tcg gga aac aac ctg acc      580
Asn Leu Glu Asn Leu Lys Leu Leu Asp Leu Ser Gly Asn Asn Leu Thr
        170                 175                 180

cac ctg ccc aag ggg ttg ctt gga gca cag gct aag ctc gag aga ctt      628
His Leu Pro Lys Gly Leu Leu Gly Ala Gln Ala Lys Leu Glu Arg Leu
    185                 190                 195

ctg ctc cac tcg aac cgc ctt gtg tct ctg gat tcg ggg ctg ttg aac      676
Leu Leu His Ser Asn Arg Leu Val Ser Leu Asp Ser Gly Leu Leu Asn
200                 205                 210                 215

agc ctg ggc gcc ctg acg gag ctg cag ttc cac cga aat cac atc cgt      724
Ser Leu Gly Ala Leu Thr Glu Leu Gln Phe His Arg Asn His Ile Arg
                220                 225                 230

tcc atc gca ccc ggg gcc ttc gac cgg ctc cca aac ctc agt tct ttg      772
Ser Ile Ala Pro Gly Ala Phe Asp Arg Leu Pro Asn Leu Ser Ser Leu
            235                 240                 245

acg ctt tcg aga aac cac ctt gcg ttt ctc ccc tct gcg ctc ttt ctt      820
Thr Leu Ser Arg Asn His Leu Ala Phe Leu Pro Ser Ala Leu Phe Leu
        250                 255                 260

cat tcg cac aat ctg act ctg ttg act ctg ttc gag aac ccg ctg gca      868
His Ser His Asn Leu Thr Leu Leu Thr Leu Phe Glu Asn Pro Leu Ala
    265                 270                 275

gag ctc ccg ggg gtg ctc ttc ggg gag atg ggg ggc ctg cag gag ctg      916
Glu Leu Pro Gly Val Leu Phe Gly Glu Met Gly Gly Leu Gln Glu Leu
280                 285                 290                 295

tgg ctg aac cgc acc cag ctg cgc acc ctg ccc gcc gcc gcc ttc cgc      964
Trp Leu Asn Arg Thr Gln Leu Arg Thr Leu Pro Ala Ala Ala Phe Arg
                300                 305                 310

aac ctg agc cgc ctg cgg tac tta ggg gtg act ctg agc ccg cgg ctg     1012
Asn Leu Ser Arg Leu Arg Tyr Leu Gly Val Thr Leu Ser Pro Arg Leu
            315                 320                 325

agc gcg ctt ccg cag ggc gcc ttc cag ggc ctt ggc gag ctc cag gtg     1060
Ser Ala Leu Pro Gln Gly Ala Phe Gln Gly Leu Gly Glu Leu Gln Val
        330                 335                 340

ctc gcc ctg cac tcc aac ggc ctg acc gcc ctc ccc gac ggc ttg ctg     1108
Leu Ala Leu His Ser Asn Gly Leu Thr Ala Leu Pro Asp Gly Leu Leu
    345                 350                 355

cgc ggc ctc ggc aag ctg cgc cag gtg tcc ctg cgc cgc aac agg ctg     1156
Arg Gly Leu Gly Lys Leu Arg Gln Val Ser Leu Arg Arg Asn Arg Leu
360                 365                 370                 375

cgc gcc ctg ccc cgt gcc ctc ttc cgc aat ctc agc agc ctg gag agc     1204
Arg Ala Leu Pro Arg Ala Leu Phe Arg Asn Leu Ser Ser Leu Glu Ser
                380                 385                 390

gtc cag ctc gac cac aac cag ctg gag acc ctg cct ggc gac gtg ttt     1252
Val Gln Leu Asp His Asn Gln Leu Glu Thr Leu Pro Gly Asp Val Phe
            395                 400                 405
```

-continued

```
ggg gct ctg ccc cgg ctg acg gag gtc ctg ttg ggg cac aac tcc tgg     1300
Gly Ala Leu Pro Arg Leu Thr Glu Val Leu Leu Gly His Asn Ser Trp
        410                 415                 420

cgc tgc gac tgt ggc ctg ggg ccc ttc ctg ggg tgg ctg cgg cag cac     1348
Arg Cys Asp Cys Gly Leu Gly Pro Phe Leu Gly Trp Leu Arg Gln His
    425                 430                 435

cta ggc ctc gtg ggc ggg gaa gag ccc cca cgg tgc gca ggc cct ggg     1396
Leu Gly Leu Val Gly Gly Glu Glu Pro Pro Arg Cys Ala Gly Pro Gly
440                 445                 450                 455

gcg cac gcc ggc ctg ccg ctc tgg gcc ctg ccg ggg ggt gac gcg gag     1444
Ala His Ala Gly Leu Pro Leu Trp Ala Leu Pro Gly Gly Asp Ala Glu
                460                 465                 470

tgc ccg ggc ccc cgg ggc ccg cct ccc cgc ccc gct gcg gac agc tcc     1492
Cys Pro Gly Pro Arg Gly Pro Pro Pro Arg Pro Ala Ala Asp Ser Ser
            475                 480                 485

tcg gaa gcc cct gtc cac cca gcc ttg gct ccc aac agc tca gaa ccc     1540
Ser Glu Ala Pro Val His Pro Ala Leu Ala Pro Asn Ser Ser Glu Pro
        490                 495                 500

tgg gtg tgg gcc cag ccg gtg acc acg ggc aaa ggt caa gat cat agt     1588
Trp Val Trp Ala Gln Pro Val Thr Thr Gly Lys Gly Gln Asp His Ser
    505                 510                 515

ccg ttc tgg ggg ttt tat ttt ctg ctt tta gct gtt cag gcc atg atc     1636
Pro Phe Trp Gly Phe Tyr Phe Leu Leu Leu Ala Val Gln Ala Met Ile
520                 525                 530                 535

acc gtg atc atc gtg ttt gct atg att aaa att ggc caa ctc ttt cga     1684
Thr Val Ile Ile Val Phe Ala Met Ile Lys Ile Gly Gln Leu Phe Arg
                540                 545                 550

aaa tta atc aga gag aga gcc ctt ggg taaaccaatg ggaaaatctt           1731
Lys Leu Ile Arg Glu Arg Ala Leu Gly
            555                 560

ctaattactt agaacctgac cagatgtggc tcggaggga atccagaccc gctgctgtct    1791

tgctctccct cccctcccca ctcctcctct cttcttcctc ttctctctca ctgccacgcc   1851

ttcctttccc tcctcctccc cctctccgct ctgtgctctt cattctcaca ggcccgcaac   1911

ccctcctctc tgtgtccccc gcccgttcct ggaaactgag cttgacgttt gtaaactgtg   1971

gttgcctgcc ttccccagct cccacgcggg tgtgcgctga cactgccggg ggcgctggac   2031

tgtgttggac ccatccgtgc tccgctgtgc ctggcttggc gtctggtgga gagaggggcc   2091

tcttcagtgt ctactgagta aggggacagc tccaggccgg ggcctgtctc ctgcacagag   2151

taagccggta aatgtttgtg aaatcaatgc gtggataaag gaacacatgc catccaagtg   2211

atgatggctt ttcctggagg gaaaggatag gctgttgctc tatctaattt tttgtttttg   2271

tttttggaca gtctagctct gtggcccagg ctggcgtgca gtgggccgtc tcagttcact   2331

gcagcctccg cctcccaggt tcaagtgatt ctcatgcctc agcgttctga gtagctggga   2391

ttagaggcgt gtgccactac acccggctaa tttttgtact ttttaaagta gagacggggc   2451

tttgccatat tggcctggct gatctcaaac tcctggtctt gaactcctgg ccacaagtga   2511

tctgcccgcc ttggcctccc aaagtgctgg gattacaggc gtaagccact acacctggcc   2571

ctcttcatcg aattttattt gagaagtaga gctcttgcca ttttttccct tgctccattt   2631

ttctcacttt atgtctctct gacctatggg ctacttggga gagcactgga ctccattcat   2691

gcatgagcat tttcaggata agcgacttct gtgaggctga gagaggaaga aaacacggag   2751

ccttccctcc aggtgcccag tgtaggtcca gcgtgtttcc tgagcctcct gtgagtttcc   2811

acttgcttta catccatgca acatgtcatt ttgaaactgg attgatttgc atttcctgga   2871

actctgccac ctcatttcac aagcatttat ggagcagtta acatgtgact ggtattcatg   2931
```

```
aatataatga taagcttgat tctagttcag ctgctgtcac agtctcattt gttcttccaa   2991

ctgaaagccg taaaaccttt gttgctttaa ttgaatgtct gtgcttatga gaggcagtgg   3051

ttaaaacagg ggctggcgag ttgacaactg tgggttcaaa tcccagctct accacttact   3111

aactgcatgg gactttgggt aagacacctg cttacattct ctaagccttg gtttcctgaa   3171

ccttaaaaca ggataacata gtacctgctt cgtagagttt ttgtgagaat taaaggcaat   3231

aaagcatata atgacttagc ccagcggcct gcaggcaata catgttaatg aatgttagct   3291

attattacta aaggatgagc aattattatt ggcatcatga tttctaaaga agagctttga   3351

gttggtattt ttctctgtgt ataagggtaa gtccgaactt tctcagactg gaggttacat   3411

tcacatcagt ctgtcttccc ctgcggatgg cctcagccct gggtggccag actctgtgct   3471

cacaatccag agcaatggat cc                                             3493
```

```
<210> SEQ ID NO 6
<211> LENGTH: 560
<212> TYPE: PRT
<213> ORGANISM: Homo sapiens

<400> SEQUENCE: 6

Met Leu Arg Gly Thr Leu Leu Cys Ala Val Leu Gly Leu Leu Arg Ala
1               5                   10                  15

Gln Pro Phe Pro Cys Pro Pro Ala Cys Lys Cys Val Phe Arg Asp Ala
            20                  25                  30

Ala Gln Cys Ser Gly Gly Asp Val Ala Arg Ile Ser Ala Leu Gly Leu
        35                  40                  45

Pro Thr Asn Leu Thr His Ile Leu Leu Phe Gly Met Gly Arg Gly Val
    50                  55                  60

Leu Gln Ser Gln Ser Phe Ser Gly Met Thr Val Leu Gln Arg Leu Met
65                  70                  75                  80

Ile Ser Asp Ser His Ile Ser Ala Val Ala Pro Gly Thr Phe Ser Asp
                85                  90                  95

Leu Ile Lys Leu Lys Thr Leu Arg Leu Ser Arg Asn Lys Ile Thr His
            100                 105                 110

Leu Pro Gly Ala Leu Leu Asp Lys Met Val Leu Leu Glu Gln Leu Phe
        115                 120                 125

Leu Asp His Asn Ala Leu Arg Gly Ile Asp Gln Asn Met Phe Gln Lys
    130                 135                 140

Leu Val Asn Leu Gln Glu Leu Ala Leu Asn Gln Asn Gln Leu Asp Phe
145                 150                 155                 160

Leu Pro Ala Ser Leu Phe Thr Asn Leu Glu Asn Leu Lys Leu Leu Asp
                165                 170                 175

Leu Ser Gly Asn Asn Leu Thr His Leu Pro Lys Gly Leu Leu Gly Ala
            180                 185                 190

Gln Ala Lys Leu Glu Arg Leu Leu Leu His Ser Asn Arg Leu Val Ser
        195                 200                 205

Leu Asp Ser Gly Leu Leu Asn Ser Leu Gly Ala Leu Thr Glu Leu Gln
    210                 215                 220

Phe His Arg Asn His Ile Arg Ser Ile Ala Pro Gly Ala Phe Asp Arg
225                 230                 235                 240

Leu Pro Asn Leu Ser Ser Leu Thr Leu Ser Arg Asn His Leu Ala Phe
                245                 250                 255

Leu Pro Ser Ala Leu Phe Leu His Ser His Asn Leu Thr Leu Leu Thr
            260                 265                 270
```

```
Leu Phe Glu Asn Pro Leu Ala Glu Leu Pro Gly Val Leu Phe Gly Glu
        275                 280                 285

Met Gly Gly Leu Gln Glu Leu Trp Leu Asn Arg Thr Gln Leu Arg Thr
    290                 295                 300

Leu Pro Ala Ala Ala Phe Arg Asn Leu Ser Arg Leu Arg Tyr Leu Gly
305                 310                 315                 320

Val Thr Leu Ser Pro Arg Leu Ser Ala Leu Pro Gln Gly Ala Phe Gln
                325                 330                 335

Gly Leu Gly Glu Leu Gln Val Leu Ala Leu His Ser Asn Gly Leu Thr
            340                 345                 350

Ala Leu Pro Asp Gly Leu Leu Arg Gly Leu Gly Lys Leu Arg Gln Val
        355                 360                 365

Ser Leu Arg Arg Asn Arg Leu Arg Ala Leu Pro Arg Ala Leu Phe Arg
    370                 375                 380

Asn Leu Ser Ser Leu Glu Ser Val Gln Leu Asp His Asn Gln Leu Glu
385                 390                 395                 400

Thr Leu Pro Gly Asp Val Phe Gly Ala Leu Pro Arg Leu Thr Glu Val
                405                 410                 415

Leu Leu Gly His Asn Ser Trp Arg Cys Asp Cys Gly Leu Gly Pro Phe
            420                 425                 430

Leu Gly Trp Leu Arg Gln His Leu Gly Leu Val Gly Gly Glu Glu Pro
        435                 440                 445

Pro Arg Cys Ala Gly Pro Gly Ala His Ala Gly Leu Pro Leu Trp Ala
    450                 455                 460

Leu Pro Gly Gly Asp Ala Glu Cys Pro Gly Pro Arg Gly Pro Pro Pro
465                 470                 475                 480

Arg Pro Ala Ala Asp Ser Ser Ser Glu Ala Pro Val His Pro Ala Leu
                485                 490                 495

Ala Pro Asn Ser Ser Glu Pro Trp Val Trp Ala Gln Pro Val Thr Thr
            500                 505                 510

Gly Lys Gly Gln Asp His Ser Pro Phe Trp Gly Phe Tyr Phe Leu Leu
        515                 520                 525

Leu Ala Val Gln Ala Met Ile Thr Val Ile Ile Val Phe Ala Met Ile
    530                 535                 540

Lys Ile Gly Gln Leu Phe Arg Lys Leu Ile Arg Glu Arg Ala Leu Gly
545                 550                 555                 560


<210> SEQ ID NO 7
<211> LENGTH: 900
<212> TYPE: DNA
<213> ORGANISM: Homo sapiens
<220> FEATURE:
<221> NAME/KEY: CDS
<222> LOCATION: (188)..(718)

<400> SEQUENCE: 7

gccaggacct ttcaggccag acaggagcac ctgaccaaag gcttcacagc cgccctcacc      60

gcccggcctt ctacggtgtc cagagacagt tagccaggcc tgggctgggc acactccacc     120

ttccctagtc accagctggt ttcccagagg agaaggctga gacccgagaa gggagccagc     180

ctgtccc atg cct gcc tgg gga gcc ctg ttc ctg ctc tgg gcc aca gca       229
        Met Pro Ala Trp Gly Ala Leu Phe Leu Leu Trp Ala Thr Ala
        1               5                   10

gag gcc acc aag gac tgc ccc agc cca tgt acc tgc cgc gcc ctg gaa       277
Glu Ala Thr Lys Asp Cys Pro Ser Pro Cys Thr Cys Arg Ala Leu Glu
15                  20                  25                  30
```

```
acc atg ggg ctg tgg gtg gac tgc agg ggc cac gga ctc acg gcc ctg      325
Thr Met Gly Leu Trp Val Asp Cys Arg Gly His Gly Leu Thr Ala Leu
                35                  40                  45

cct gcc ctg ccg gcc cgc acc cgc cac ctt ctg ctg gcc aac aac agc      373
Pro Ala Leu Pro Ala Arg Thr Arg His Leu Leu Leu Ala Asn Asn Ser
            50                  55                  60

ctt cag tcc gtg ccc ccg gga gcc ttt gac cac ctg ccc cag ctg cag      421
Leu Gln Ser Val Pro Pro Gly Ala Phe Asp His Leu Pro Gln Leu Gln
        65                  70                  75

acc ctc gat gtg acg cag aac ccc tgg cac tgt gac tgc agc ctc acc      469
Thr Leu Asp Val Thr Gln Asn Pro Trp His Cys Asp Cys Ser Leu Thr
    80                  85                  90

tat ctg cgc ctc tgg ctg gag gac cgc acg ccc gag gcc ctg ctg cag      517
Tyr Leu Arg Leu Trp Leu Glu Asp Arg Thr Pro Glu Ala Leu Leu Gln
95                  100                 105                 110

gtc cgc tgt gcc agc ccc agc ctc gct gcc cat ggc ccg ctg ggc cgg      565
Val Arg Cys Ala Ser Pro Ser Leu Ala Ala His Gly Pro Leu Gly Arg
                115                 120                 125

ctg aca ggc tac cag ctg ggc agc tgt ggc tgg cag ctg cag gcg tcc      613
Leu Thr Gly Tyr Gln Leu Gly Ser Cys Gly Trp Gln Leu Gln Ala Ser
            130                 135                 140

tgg gtg cgc ccg ggg gtc ttg tgg gac gtg gcg ctg gtc gcc gtg gcc      661
Trp Val Arg Pro Gly Val Leu Trp Asp Val Ala Leu Val Ala Val Ala
        145                 150                 155

gcg ctg ggc ctg gct ctt ctg gct ggc ctg ctg tgt gcc acc aca gag      709
Ala Leu Gly Leu Ala Leu Leu Ala Gly Leu Leu Cys Ala Thr Thr Glu
    160                 165                 170

gcc ctg gat tgagccaggc cccagaacc cctggctcca ggccaggggg               758
Ala Leu Asp
175

ccagtccctg aggcaggtcc ccagactcca ccaagcctgg tcagcccaaa ccaccagaag    818

cccagaataa actggcagct cagctgtttt atataaaaaa aaaaaaaaaa aaaaaaaaaa    878

aaaaaaaaaa aaaaaaaaaa aa                                              900


<210> SEQ ID NO 8
<211> LENGTH: 177
<212> TYPE: PRT
<213> ORGANISM: Homo sapiens

<400> SEQUENCE: 8

Met Pro Ala Trp Gly Ala Leu Phe Leu Leu Trp Ala Thr Ala Glu Ala
1               5                   10                  15

Thr Lys Asp Cys Pro Ser Pro Cys Thr Cys Arg Ala Leu Glu Thr Met
            20                  25                  30

Gly Leu Trp Val Asp Cys Arg Gly His Gly Leu Thr Ala Leu Pro Ala
        35                  40                  45

Leu Pro Ala Arg Thr Arg His Leu Leu Leu Ala Asn Asn Ser Leu Gln
    50                  55                  60

Ser Val Pro Pro Gly Ala Phe Asp His Leu Pro Gln Leu Gln Thr Leu
65                  70                  75                  80

Asp Val Thr Gln Asn Pro Trp His Cys Asp Cys Ser Leu Thr Tyr Leu
                85                  90                  95

Arg Leu Trp Leu Glu Asp Arg Thr Pro Glu Ala Leu Leu Gln Val Arg
            100                 105                 110

Cys Ala Ser Pro Ser Leu Ala Ala His Gly Pro Leu Gly Arg Leu Thr
        115                 120                 125
```

```
Gly Tyr Gln Leu Gly Ser Cys Gly Trp Gln Leu Gln Ala Ser Trp Val
    130                 135                 140

Arg Pro Gly Val Leu Trp Asp Val Ala Leu Val Ala Val Ala Ala Leu
145                 150                 155                 160

Gly Leu Ala Leu Leu Ala Gly Leu Leu Cys Ala Thr Thr Glu Ala Leu
                165                 170                 175

Asp


<210> SEQ ID NO 9
<211> LENGTH: 8833
<212> TYPE: DNA
<213> ORGANISM: Homo sapiens
<220> FEATURE:
<221> NAME/KEY: CDS
<222> LOCATION: (251)..(8689)

<400> SEQUENCE: 9

agctcacagc tattgtggtg ggaaagggag ggtggttggt ggatgtcaca gcttgggctt      60

tatctccccc agcagtgggg actccacagc ccctgggcta cataacagca agacagtccg     120

gagctgtagc agacctgatt gagcctttgc agcagctgag agcatggcct agggtgggcg     180

gcaccattgt ccagcagctg agtttcccag ggaccttgga gatagccgca gccctcattt     240

gcaggggaag atg att cct gcc aga ttt gcc ggg gtg ctg ctt gct ctg        289
           Met Ile Pro Ala Arg Phe Ala Gly Val Leu Leu Ala Leu
           1               5                   10

gcc ctc att ttg cca ggg acc ctt tgt gca gaa gga act cgc ggc agg        337
Ala Leu Ile Leu Pro Gly Thr Leu Cys Ala Glu Gly Thr Arg Gly Arg
    15                  20                  25

tca tcc acg gcc cga tgc agc ctt ttc gga agt gac ttc gtc aac acc        385
Ser Ser Thr Ala Arg Cys Ser Leu Phe Gly Ser Asp Phe Val Asn Thr
30                  35                  40                  45

ttt gat ggg agc atg tac agc ttt gcg gga tac tgc agt tac ctc ctg        433
Phe Asp Gly Ser Met Tyr Ser Phe Ala Gly Tyr Cys Ser Tyr Leu Leu
                50                  55                  60

gca ggg ggc tgc cag aaa cgc tcc ttc tcg att att ggg gac ttc cag        481
Ala Gly Gly Cys Gln Lys Arg Ser Phe Ser Ile Ile Gly Asp Phe Gln
            65                  70                  75

aat ggc aag aga gtg agc ctc tcc gtg tat ctt ggg gaa ttt ttt gac        529
Asn Gly Lys Arg Val Ser Leu Ser Val Tyr Leu Gly Glu Phe Phe Asp
        80                  85                  90

atc cat ttg ttt gtc aat ggt acc gtg aca cag ggg gac caa aga gtc        577
Ile His Leu Phe Val Asn Gly Thr Val Thr Gln Gly Asp Gln Arg Val
    95                  100                 105

tcc atg ccc tat gcc tcc aaa ggg ctg tat cta gaa act gag gct ggg        625
Ser Met Pro Tyr Ala Ser Lys Gly Leu Tyr Leu Glu Thr Glu Ala Gly
110                 115                 120                 125

tac tac aag ctg tcc ggt gag gcc tat ggc ttt gtg gcc agg atc gat        673
Tyr Tyr Lys Leu Ser Gly Glu Ala Tyr Gly Phe Val Ala Arg Ile Asp
                130                 135                 140

ggc agc ggc aac ttt caa gtc ctg ctg tca gac aga tac ttc aac aag        721
Gly Ser Gly Asn Phe Gln Val Leu Leu Ser Asp Arg Tyr Phe Asn Lys
            145                 150                 155

acc tgc ggg ctg tgt ggc aac ttt aac atc ttt gct gaa gat gac ttt        769
Thr Cys Gly Leu Cys Gly Asn Phe Asn Ile Phe Ala Glu Asp Asp Phe
        160                 165                 170

atg acc caa gaa ggg acc ttg acc tcg gac cct tat gac ttt gcc aac        817
Met Thr Gln Glu Gly Thr Leu Thr Ser Asp Pro Tyr Asp Phe Ala Asn
    175                 180                 185

tca tgg gct ctg agc agt gga gaa cag tgg tgt gaa cgg gca tct cct        865
```

-continued

```
Ser Trp Ala Leu Ser Ser Gly Glu Gln Trp Cys Glu Arg Ala Ser Pro
190                 195                 200                 205

ccc agc agc tca tgc aac atc tcc tct ggg gaa atg cag aag ggc ctg      913
Pro Ser Ser Ser Cys Asn Ile Ser Ser Gly Glu Met Gln Lys Gly Leu
                210                 215                 220

tgg gag cag tgc cag ctt ctg aag agc acc tcg gtg ttt gcc cgc tgc      961
Trp Glu Gln Cys Gln Leu Leu Lys Ser Thr Ser Val Phe Ala Arg Cys
            225                 230                 235

cac cct ctg gtg gac ccc gag cct ttt gtg gcc ctg tgt gag aag act     1009
His Pro Leu Val Asp Pro Glu Pro Phe Val Ala Leu Cys Glu Lys Thr
        240                 245                 250

ttg tgt gag tgt gct ggg ggg ctg gag tgc gcc tgc cct gcc ctc ctg     1057
Leu Cys Glu Cys Ala Gly Gly Leu Glu Cys Ala Cys Pro Ala Leu Leu
    255                 260                 265

gag tac gcc cgg acc tgt gcc cag gag gga atg gtg ctg tac ggc tgg     1105
Glu Tyr Ala Arg Thr Cys Ala Gln Glu Gly Met Val Leu Tyr Gly Trp
270                 275                 280                 285

acc gac cac agc gcg tgc agc cca gtg tgc cct gct ggt atg gag tat     1153
Thr Asp His Ser Ala Cys Ser Pro Val Cys Pro Ala Gly Met Glu Tyr
                290                 295                 300

agg cag tgt gtg tcc cct tgc gcc agg acc tgc cag agc ctg cac atc     1201
Arg Gln Cys Val Ser Pro Cys Ala Arg Thr Cys Gln Ser Leu His Ile
            305                 310                 315

aat gaa atg tgt cag gag cga tgc gtg gat ggc tgc agc tgc cct gag     1249
Asn Glu Met Cys Gln Glu Arg Cys Val Asp Gly Cys Ser Cys Pro Glu
        320                 325                 330

gga cag ctc ctg gat gaa ggc ctc tgc gtg gag agc acc gag tgt ccc     1297
Gly Gln Leu Leu Asp Glu Gly Leu Cys Val Glu Ser Thr Glu Cys Pro
    335                 340                 345

tgc gtg cat tcc gga aag cgc tac cct ccc ggc acc tcc ctc tct cga     1345
Cys Val His Ser Gly Lys Arg Tyr Pro Pro Gly Thr Ser Leu Ser Arg
350                 355                 360                 365

gac tgc aac acc tgc att tgc cga aac agc cag tgg atc tgc agc aat     1393
Asp Cys Asn Thr Cys Ile Cys Arg Asn Ser Gln Trp Ile Cys Ser Asn
                370                 375                 380

gaa gaa tgt cca ggg gag tgc ctt gtc aca ggt caa tca cac ttc aag     1441
Glu Glu Cys Pro Gly Glu Cys Leu Val Thr Gly Gln Ser His Phe Lys
            385                 390                 395

agc ttt gac aac aga tac ttc acc ttc agt ggg atc tgc cag tac ctg     1489
Ser Phe Asp Asn Arg Tyr Phe Thr Phe Ser Gly Ile Cys Gln Tyr Leu
        400                 405                 410

ctg gcc cgg gat tgc cag gac cac tcc ttc tcc att gtc att gag act     1537
Leu Ala Arg Asp Cys Gln Asp His Ser Phe Ser Ile Val Ile Glu Thr
    415                 420                 425

gtc cag tgt gct gat gac cgc gac gct gtg tgc acc cgc tcc gtc acc     1585
Val Gln Cys Ala Asp Asp Arg Asp Ala Val Cys Thr Arg Ser Val Thr
430                 435                 440                 445

gtc cgg ctg cct ggc ctg cac aac agc ctt gtg aaa ctg aag cat ggg     1633
Val Arg Leu Pro Gly Leu His Asn Ser Leu Val Lys Leu Lys His Gly
                450                 455                 460

gca gga gtt gcc atg gat ggc cag gac gtc cag ctc ccc ctc ctg aaa     1681
Ala Gly Val Ala Met Asp Gly Gln Asp Val Gln Leu Pro Leu Leu Lys
            465                 470                 475

ggt gac ctc cgc atc cag cat aca gtg acg gcc tcc gtg cgc ctc agc     1729
Gly Asp Leu Arg Ile Gln His Thr Val Thr Ala Ser Val Arg Leu Ser
        480                 485                 490

tac ggg gag gac ctg cag atg gac tgg gat ggc cgc ggg agg ctg ctg     1777
Tyr Gly Glu Asp Leu Gln Met Asp Trp Asp Gly Arg Gly Arg Leu Leu
    495                 500                 505
```

```
gtg aag ctg tcc ccc gtc tat gcc ggg aag acc tgc ggc ctg tgt ggg     1825
Val Lys Leu Ser Pro Val Tyr Ala Gly Lys Thr Cys Gly Leu Cys Gly
510                 515                 520                 525

aat tac aat ggc aac cag ggc gac gac ttc ctt acc ccc tct ggg ctg     1873
Asn Tyr Asn Gly Asn Gln Gly Asp Asp Phe Leu Thr Pro Ser Gly Leu
                530                 535                 540

gcg gag ccc cgg gtg gag gac ttc ggg aac gcc tgg aag ctg cac ggg     1921
Ala Glu Pro Arg Val Glu Asp Phe Gly Asn Ala Trp Lys Leu His Gly
            545                 550                 555

gac tgc cag gac ctg cag aag cag cac agc gat ccc tgc gcc ctc aac     1969
Asp Cys Gln Asp Leu Gln Lys Gln His Ser Asp Pro Cys Ala Leu Asn
        560                 565                 570

ccg cgc atg acc agg ttc tcc gag gag gcg tgc gcg gtc ctg acg tcc     2017
Pro Arg Met Thr Arg Phe Ser Glu Glu Ala Cys Ala Val Leu Thr Ser
    575                 580                 585

ccc aca ttc gag gcc tgc cat cgt gcc gtc agc ccg ctg ccc tac ctg     2065
Pro Thr Phe Glu Ala Cys His Arg Ala Val Ser Pro Leu Pro Tyr Leu
590                 595                 600                 605

cgg aac tgc cgc tac gac gtg tgc tcc tgc tcg gac ggc cgc gag tgc     2113
Arg Asn Cys Arg Tyr Asp Val Cys Ser Cys Ser Asp Gly Arg Glu Cys
                610                 615                 620

ctg tgc ggc gcc ctg gcc agc tat gcc gcg gcc tgc gcg ggg aga ggc     2161
Leu Cys Gly Ala Leu Ala Ser Tyr Ala Ala Ala Cys Ala Gly Arg Gly
            625                 630                 635

gtg cgc gtc gcg tgg cgc gag cca ggc cgc tgt gag ctg aac tgc ccg     2209
Val Arg Val Ala Trp Arg Glu Pro Gly Arg Cys Glu Leu Asn Cys Pro
        640                 645                 650

aaa ggc cag gtg tac ctg cag tgc ggg acc ccc tgc aac ctg acc tgc     2257
Lys Gly Gln Val Tyr Leu Gln Cys Gly Thr Pro Cys Asn Leu Thr Cys
    655                 660                 665

cgc tct ctc tct tac ccg gat gag gaa tgc aat gag gcc tgc ctg gag     2305
Arg Ser Leu Ser Tyr Pro Asp Glu Glu Cys Asn Glu Ala Cys Leu Glu
670                 675                 680                 685

ggc tgc ttc tgc ccc cca ggg ctc tac atg gat gag agg ggg gac tgc     2353
Gly Cys Phe Cys Pro Pro Gly Leu Tyr Met Asp Glu Arg Gly Asp Cys
                690                 695                 700

gtg ccc aag gcc cag tgc ccc tgt tac tat gac ggt gag atc ttc cag     2401
Val Pro Lys Ala Gln Cys Pro Cys Tyr Tyr Asp Gly Glu Ile Phe Gln
            705                 710                 715

cca gaa gac atc ttc tca gac cat cac acc atg tgc tac tgt gag gat     2449
Pro Glu Asp Ile Phe Ser Asp His His Thr Met Cys Tyr Cys Glu Asp
        720                 725                 730

ggc ttc atg cac tgt acc atg agt gga gtc ccc gga agc ttg ctg cct     2497
Gly Phe Met His Cys Thr Met Ser Gly Val Pro Gly Ser Leu Leu Pro
    735                 740                 745

gac gct gtc ctc agc agt ccc ctg tct cat cgc agc aaa agg agc cta     2545
Asp Ala Val Leu Ser Ser Pro Leu Ser His Arg Ser Lys Arg Ser Leu
750                 755                 760                 765

tcc tgt cgg ccc ccc atg gtc aag ctg gtg tgt ccc gct gac aac ctg     2593
Ser Cys Arg Pro Pro Met Val Lys Leu Val Cys Pro Ala Asp Asn Leu
                770                 775                 780

cgg gct gaa ggg ctc gag tgt acc aaa acg tgc cag aac tat gac ctg     2641
Arg Ala Glu Gly Leu Glu Cys Thr Lys Thr Cys Gln Asn Tyr Asp Leu
            785                 790                 795

gag tgc atg agc atg ggc tgt gtc tct ggc tgc ctc tgc ccc ccg ggc     2689
Glu Cys Met Ser Met Gly Cys Val Ser Gly Cys Leu Cys Pro Pro Gly
        800                 805                 810

atg gtc cgg cat gag aac aga tgt gtg gcc ctg gaa agg tgt ccc tgc     2737
Met Val Arg His Glu Asn Arg Cys Val Ala Leu Glu Arg Cys Pro Cys
    815                 820                 825
```

```
ttc cat cag ggc aag gag tat gcc cct gga gaa aca gtg aag att ggc      2785
Phe His Gln Gly Lys Glu Tyr Ala Pro Gly Glu Thr Val Lys Ile Gly
830                 835                 840                 845

tgc aac act tgt gtc tgt cgg gac cgg aag tgg aac tgc aca gac cat      2833
Cys Asn Thr Cys Val Cys Arg Asp Arg Lys Trp Asn Cys Thr Asp His
                850                 855                 860

gtg tgt gat gcc acg tgc tcc acg atc ggc atg gcc cac tac ctc acc      2881
Val Cys Asp Ala Thr Cys Ser Thr Ile Gly Met Ala His Tyr Leu Thr
            865                 870                 875

ttc gac ggg ctc aaa tac ctg ttc ccc ggg gag tgc cag tac gtt ctg      2929
Phe Asp Gly Leu Lys Tyr Leu Phe Pro Gly Glu Cys Gln Tyr Val Leu
        880                 885                 890

gtg cag gat tac tgc ggc agt aac cct ggg acc ttt cgg atc cta gtg      2977
Val Gln Asp Tyr Cys Gly Ser Asn Pro Gly Thr Phe Arg Ile Leu Val
    895                 900                 905

ggg aat aag gga tgc agc cac ccc tca gtg aaa tgc aag aaa cgg gtc      3025
Gly Asn Lys Gly Cys Ser His Pro Ser Val Lys Cys Lys Lys Arg Val
910                 915                 920                 925

acc atc ctg gtg gag gga gga gag att gag ctg ttt gac ggg gag gtg      3073
Thr Ile Leu Val Glu Gly Gly Glu Ile Glu Leu Phe Asp Gly Glu Val
                930                 935                 940

aat gtg aag agg ccc atg aag gat gag act cac ttt gag gtg gtg gag      3121
Asn Val Lys Arg Pro Met Lys Asp Glu Thr His Phe Glu Val Val Glu
            945                 950                 955

tct ggc cgg tac atc att ctg ctg ctg ggc aaa gcc ctc tcc gtg gtc      3169
Ser Gly Arg Tyr Ile Ile Leu Leu Leu Gly Lys Ala Leu Ser Val Val
        960                 965                 970

tgg gac cgc cac ctg agc atc tcc gtg gtc ctg aag cag aca tac cag      3217
Trp Asp Arg His Leu Ser Ile Ser Val Val Leu Lys Gln Thr Tyr Gln
    975                 980                 985

gag aaa gtg tgt ggc ctg tgt ggg aat ttt gat  ggc atc cag aac aat     3265
Glu Lys Val Cys Gly Leu Cys Gly Asn Phe Asp  Gly Ile Gln Asn Asn
990                 995                 1000                1005

gac ctc acc agc agc  aac ctc caa gtg gag  gaa gac cct gtg gac        3310
Asp Leu Thr Ser Ser  Asn Leu Gln Val Glu  Glu Asp Pro Val Asp
                1010                 1015                 1020

ttt ggg aac tcc tgg  aaa gtg agc tcg cag  tgt gct gac acc aga        3355
Phe Gly Asn Ser Trp  Lys Val Ser Ser Gln  Cys Ala Asp Thr Arg
                1025                 1030                 1035

aaa gtg cct ctg gac  tca tcc cct gcc acc  tgc cat aac aac atc        3400
Lys Val Pro Leu Asp  Ser Ser Pro Ala Thr  Cys His Asn Asn Ile
                1040                 1045                 1050

atg aag cag acg atg  gtg gat tcc tcc tgt  aga atc ctt acc agt        3445
Met Lys Gln Thr Met  Val Asp Ser Ser Cys  Arg Ile Leu Thr Ser
                1055                 1060                 1065

gac gtc ttc cag gac  tgc aac aag ctg gtg  gac ccc gag cca tat        3490
Asp Val Phe Gln Asp  Cys Asn Lys Leu Val  Asp Pro Glu Pro Tyr
                1070                 1075                 1080

ctg gat gtc tgc att  tac gac acc tgc tcc  tgt gag tcc att ggg        3535
Leu Asp Val Cys Ile  Tyr Asp Thr Cys Ser  Cys Glu Ser Ile Gly
                1085                 1090                 1095

gac tgc gcc tgc ttc  tgc gac acc att gct  gcc tat gcc cac gtg        3580
Asp Cys Ala Cys Phe  Cys Asp Thr Ile Ala  Ala Tyr Ala His Val
                1100                 1105                 1110

tgt gcc cag cat ggc  aag gtg gtg acc tgg  agg acg gcc aca ttg        3625
Cys Ala Gln His Gly  Lys Val Val Thr Trp  Arg Thr Ala Thr Leu
                1115                 1120                 1125

tgc ccc cag agc tgc  gag gag agg aat ctc  cgg gag aac ggg tat        3670
Cys Pro Gln Ser Cys  Glu Glu Arg Asn Leu  Arg Glu Asn Gly Tyr
```

```
                1130                1135                1140

gag tgt gag tgg cgc  tat aac agc tgt gca  cct gcc tgt caa gtc       3715
Glu Cys Glu Trp Arg  Tyr Asn Ser Cys Ala  Pro Ala Cys Gln Val
                1145                1150                1155

acg tgt cag cac cct  gag cca ctg gcc tgc  cct gtg cag tgt gtg       3760
Thr Cys Gln His Pro  Glu Pro Leu Ala Cys  Pro Val Gln Cys Val
                1160                1165                1170

gag ggc tgc cat gcc  cac tgc cct cca ggg  aaa atc ctg gat gag       3805
Glu Gly Cys His Ala  His Cys Pro Pro Gly  Lys Ile Leu Asp Glu
                1175                1180                1185

ctt ttg cag acc tgc  gtt gac cct gaa gac  tgt cca gtg tgt gag       3850
Leu Leu Gln Thr Cys  Val Asp Pro Glu Asp  Cys Pro Val Cys Glu
                1190                1195                1200

gtg gct ggc cgg cgt  ttt gcc tca gga aag  aaa gtc acc ttg aat       3895
Val Ala Gly Arg Arg  Phe Ala Ser Gly Lys  Lys Val Thr Leu Asn
                1205                1210                1215

ccc agt gac cct gag  cac tgc cag att tgc  cac tgt gat gtt gtc       3940
Pro Ser Asp Pro Glu  His Cys Gln Ile Cys  His Cys Asp Val Val
                1220                1225                1230

aac ctc acc tgt gaa  gcc tgc cag gag ccg  gga ggc ctg gtg gtg       3985
Asn Leu Thr Cys Glu  Ala Cys Gln Glu Pro  Gly Gly Leu Val Val
                1235                1240                1245

cct ccc aca gat gcc  ccg gtg agc ccc acc  act ctg tat gtg gag       4030
Pro Pro Thr Asp Ala  Pro Val Ser Pro Thr  Thr Leu Tyr Val Glu
                1250                1255                1260

gac atc tcg gaa ccg  ccg ttg cac gat ttc  tac tgc agc agg cta       4075
Asp Ile Ser Glu Pro  Pro Leu His Asp Phe  Tyr Cys Ser Arg Leu
                1265                1270                1275

ctg gac ctg gtc ttc  ctg ctg gat ggc tcc  tcc agg ctg tcc gag       4120
Leu Asp Leu Val Phe  Leu Leu Asp Gly Ser  Ser Arg Leu Ser Glu
                1280                1285                1290

gct gag ttt gaa gtg  ctg aag gcc ttt gtg  gtg gac atg atg gag       4165
Ala Glu Phe Glu Val  Leu Lys Ala Phe Val  Val Asp Met Met Glu
                1295                1300                1305

cgg ctg cgc atc tcc  cag aag tgg gtc cgc  gtg gcc gtg gtg gag       4210
Arg Leu Arg Ile Ser  Gln Lys Trp Val Arg  Val Ala Val Val Glu
                1310                1315                1320

tac cac gac ggc tcc  cac gcc tac atc ggg  ctc aag gac cgg aag       4255
Tyr His Asp Gly Ser  His Ala Tyr Ile Gly  Leu Lys Asp Arg Lys
                1325                1330                1335

cga ccg tca gag ctg  cgg cgc att gcc agc  cag gtg aag tat gcg       4300
Arg Pro Ser Glu Leu  Arg Arg Ile Ala Ser  Gln Val Lys Tyr Ala
                1340                1345                1350

ggc agc cag gtg gcc  tcc acc agc gag gtc  ttg aaa tac aca ctg       4345
Gly Ser Gln Val Ala  Ser Thr Ser Glu Val  Leu Lys Tyr Thr Leu
                1355                1360                1365

ttc caa atc ttc agc  aag atc gac cgc cct  gaa gcc tcc cgc atc       4390
Phe Gln Ile Phe Ser  Lys Ile Asp Arg Pro  Glu Ala Ser Arg Ile
                1370                1375                1380

acc ctg ctc ctg atg  gcc agc cag gag ccc  caa cgg atg tcc cgg       4435
Thr Leu Leu Leu Met  Ala Ser Gln Glu Pro  Gln Arg Met Ser Arg
                1385                1390                1395

aac ttt gtc cgc tac  gtc cag ggc ctg aag  aag aag aag gtc att       4480
Asn Phe Val Arg Tyr  Val Gln Gly Leu Lys  Lys Lys Lys Val Ile
                1400                1405                1410

gtg atc ccg gtg ggc  att ggg ccc cat gcc  aac ctc aag cag atc       4525
Val Ile Pro Val Gly  Ile Gly Pro His Ala  Asn Leu Lys Gln Ile
                1415                1420                1425

cgc ctc atc gag aag  cag gcc cct gag aac  aag gcc ttc gtg ctg       4570
```

```
Arg Leu Ile Glu Lys  Gln Ala Pro Glu Asn  Lys Ala Phe Val Leu
                1430                 1435                 1440

agc agt gtg gat gag  ctg gag cag caa agg  gac gag atc gtt agc      4615
Ser Ser Val Asp Glu  Leu Glu Gln Gln Arg  Asp Glu Ile Val Ser
                1445                 1450                 1455

tac ctc tgt gac ctt  gcc cct gaa gcc cct  cct cct act ctg ccc      4660
Tyr Leu Cys Asp Leu  Ala Pro Glu Ala Pro  Pro Pro Thr Leu Pro
                1460                 1465                 1470

ccc gac atg gca caa  gtc act gtg ggc ccg  ggg ctc ttg ggg gtt      4705
Pro Asp Met Ala Gln  Val Thr Val Gly Pro  Gly Leu Leu Gly Val
                1475                 1480                 1485

tcg acc ctg ggg ccc  aag agg aac tcc atg  gtt ctg gat gtg gcg      4750
Ser Thr Leu Gly Pro  Lys Arg Asn Ser Met  Val Leu Asp Val Ala
                1490                 1495                 1500

ttc gtc ctg gaa gga  tcg gac aaa att ggt  gaa gcc gac ttc aac      4795
Phe Val Leu Glu Gly  Ser Asp Lys Ile Gly  Glu Ala Asp Phe Asn
                1505                 1510                 1515

agg agc aag gag ttc  atg gag gag gtg att  cag cgg atg gat gtg      4840
Arg Ser Lys Glu Phe  Met Glu Glu Val Ile  Gln Arg Met Asp Val
                1520                 1525                 1530

ggc cag gac agc atc  cac gtc acg gtg ctg  cag tac tcc tac atg      4885
Gly Gln Asp Ser Ile  His Val Thr Val Leu  Gln Tyr Ser Tyr Met
                1535                 1540                 1545

gtg act gtg gag tac  ccc ttc agc gag gca  cag tcc aaa ggg gac      4930
Val Thr Val Glu Tyr  Pro Phe Ser Glu Ala  Gln Ser Lys Gly Asp
                1550                 1555                 1560

atc ctg cag cgg gtg  cga gag atc cgc tac  cag ggc ggc aac agg      4975
Ile Leu Gln Arg Val  Arg Glu Ile Arg Tyr  Gln Gly Gly Asn Arg
                1565                 1570                 1575

acc aac act ggg ctg  gcc ctg cgg tac ctc  tct gac cac agc ttc      5020
Thr Asn Thr Gly Leu  Ala Leu Arg Tyr Leu  Ser Asp His Ser Phe
                1580                 1585                 1590

ttg gtc agc cag ggt  gac cgg gag cag gcg  ccc aac ctg gtc tac      5065
Leu Val Ser Gln Gly  Asp Arg Glu Gln Ala  Pro Asn Leu Val Tyr
                1595                 1600                 1605

atg gtc acc gga aat  cct gcc tct gat gag  atc aag agg ctg cct      5110
Met Val Thr Gly Asn  Pro Ala Ser Asp Glu  Ile Lys Arg Leu Pro
                1610                 1615                 1620

gga gac atc cag gtg  gtg ccc att gga gtg  ggc cct aat gcc aac      5155
Gly Asp Ile Gln Val  Val Pro Ile Gly Val  Gly Pro Asn Ala Asn
                1625                 1630                 1635

gtg cag gag ctg gag  agg att ggc tgg ccc  aat gcc cct atc ctc      5200
Val Gln Glu Leu Glu  Arg Ile Gly Trp Pro  Asn Ala Pro Ile Leu
                1640                 1645                 1650

atc cag gac ttt gag  acg ctc ccc cga gag  gct cct gac ctg gtg      5245
Ile Gln Asp Phe Glu  Thr Leu Pro Arg Glu  Ala Pro Asp Leu Val
                1655                 1660                 1665

ctg cag agg tgc tgc  tcc gga gag ggg ctg  cag atc ccc acc ctc      5290
Leu Gln Arg Cys Cys  Ser Gly Glu Gly Leu  Gln Ile Pro Thr Leu
                1670                 1675                 1680

tcc cct gca cct gac  tgc agc cag ccc ctg  gac gtg atc ctt ctc      5335
Ser Pro Ala Pro Asp  Cys Ser Gln Pro Leu  Asp Val Ile Leu Leu
                1685                 1690                 1695

ctg gat ggc tcc tcc  agt ttc cca gct tct  tat ttt gat gaa atg      5380
Leu Asp Gly Ser Ser  Ser Phe Pro Ala Ser  Tyr Phe Asp Glu Met
                1700                 1705                 1710

aag agt ttc gcc aag  gct ttc att tca aaa  gcc aat ata ggg cct      5425
Lys Ser Phe Ala Lys  Ala Phe Ile Ser Lys  Ala Asn Ile Gly Pro
                1715                 1720                 1725
```

```
cgt ctc act cag gtg  tca gtg ctg cag tat  gga agc atc acc acc       5470
Arg Leu Thr Gln Val  Ser Val Leu Gln Tyr  Gly Ser Ile Thr Thr
                1730                 1735                 1740

att gac gtg cca tgg  aac gtg gtc ccg gag  aaa gcc cat ttg ctg       5515
Ile Asp Val Pro Trp  Asn Val Val Pro Glu  Lys Ala His Leu Leu
                1745                 1750                 1755

agc ctt gtg gac gtc  atg cag cgg gag gga  ggc ccc agc caa atc       5560
Ser Leu Val Asp Val  Met Gln Arg Glu Gly  Gly Pro Ser Gln Ile
                1760                 1765                 1770

ggg gat gcc ttg ggc  ttt gct gtg cga tac  ttg act tca gaa atg       5605
Gly Asp Ala Leu Gly  Phe Ala Val Arg Tyr  Leu Thr Ser Glu Met
                1775                 1780                 1785

cat ggt gcc agg ccg  gga gcc tca aag gcg  gtg gtc atc ctg gtc       5650
His Gly Ala Arg Pro  Gly Ala Ser Lys Ala  Val Val Ile Leu Val
                1790                 1795                 1800

acg gac gtc tct gtg  gat tca gtg gat gca  gca gct gat gcc gcc       5695
Thr Asp Val Ser Val  Asp Ser Val Asp Ala  Ala Ala Asp Ala Ala
                1805                 1810                 1815

agg tcc aac aga gtg  aca gtg ttc cct att  gga att gga gat cgc       5740
Arg Ser Asn Arg Val  Thr Val Phe Pro Ile  Gly Ile Gly Asp Arg
                1820                 1825                 1830

tac gat gca gcc cag  cta cgg atc ttg gca  ggc cca gca ggc gac       5785
Tyr Asp Ala Ala Gln  Leu Arg Ile Leu Ala  Gly Pro Ala Gly Asp
                1835                 1840                 1845

tcc aac gtg gtg aag  ctc cag cga atc gaa  gac ctc cct acc atg       5830
Ser Asn Val Val Lys  Leu Gln Arg Ile Glu  Asp Leu Pro Thr Met
                1850                 1855                 1860

gtc acc ttg ggc aat  tcc ttc ctc cac aaa  ctg tgc tct gga ttt       5875
Val Thr Leu Gly Asn  Ser Phe Leu His Lys  Leu Cys Ser Gly Phe
                1865                 1870                 1875

gtt agg att tgc atg  gat gag gat ggg aat  gag aag agg ccc ggg       5920
Val Arg Ile Cys Met  Asp Glu Asp Gly Asn  Glu Lys Arg Pro Gly
                1880                 1885                 1890

gac gtc tgg acc ttg  cca gac cag tgc cac  acc gtg act tgc cag       5965
Asp Val Trp Thr Leu  Pro Asp Gln Cys His  Thr Val Thr Cys Gln
                1895                 1900                 1905

cca gat ggc cag acc  ttg ctg aag agt cat  cgg gtc aac tgt gac       6010
Pro Asp Gly Gln Thr  Leu Leu Lys Ser His  Arg Val Asn Cys Asp
                1910                 1915                 1920

cgg ggg ctg agg cct  tcg tgc cct aac agc  cag tcc cct gtt aaa       6055
Arg Gly Leu Arg Pro  Ser Cys Pro Asn Ser  Gln Ser Pro Val Lys
                1925                 1930                 1935

gtg gaa gag acc tgt  ggc tgc cgc tgg acc  tgc ccc tgc gtg tgc       6100
Val Glu Glu Thr Cys  Gly Cys Arg Trp Thr  Cys Pro Cys Val Cys
                1940                 1945                 1950

aca ggc agc tcc act  cgg cac atc gtg acc  ttt gat ggg cag aat       6145
Thr Gly Ser Ser Thr  Arg His Ile Val Thr  Phe Asp Gly Gln Asn
                1955                 1960                 1965

ttc aag ctg act ggc  agc tgt tct tat gtc  cta ttt caa aac aag       6190
Phe Lys Leu Thr Gly  Ser Cys Ser Tyr Val  Leu Phe Gln Asn Lys
                1970                 1975                 1980

gag cag gac ctg gag  gtg att ctc cat aat  ggt gcc tgc agc cct       6235
Glu Gln Asp Leu Glu  Val Ile Leu His Asn  Gly Ala Cys Ser Pro
                1985                 1990                 1995

gga gca agg cag ggc  tgc atg aaa tcc atc  gag gtg aag cac agt       6280
Gly Ala Arg Gln Gly  Cys Met Lys Ser Ile  Glu Val Lys His Ser
                2000                 2005                 2010

gcc ctc tcc gtc gag  ctg cac agt gac atg  gag gtg acg gtg aat       6325
Ala Leu Ser Val Glu  Leu His Ser Asp Met  Glu Val Thr Val Asn
                2015                 2020                 2025
```

```
ggg aga ctg gtc tct  gtt cct tac gtg ggt  ggg aac atg gaa gtc       6370
Gly Arg Leu Val Ser  Val Pro Tyr Val Gly  Gly Asn Met Glu Val
                2030                 2035                 2040

aac gtt tat ggt gcc  atc atg cat gag gtc  aga ttc aat cac ctt       6415
Asn Val Tyr Gly Ala  Ile Met His Glu Val  Arg Phe Asn His Leu
                2045                 2050                 2055

ggt cac atc ttc aca  ttc act cca caa aac  aat gag ttc caa ctg       6460
Gly His Ile Phe Thr  Phe Thr Pro Gln Asn  Asn Glu Phe Gln Leu
                2060                 2065                 2070

cag ctc agc ccc aag  act ttt gct tca aag  acg tat ggt ctg tgt       6505
Gln Leu Ser Pro Lys  Thr Phe Ala Ser Lys  Thr Tyr Gly Leu Cys
                2075                 2080                 2085

ggg atc tgt gat gag  aac gga gcc aat gac  ttc atg ctg agg gat       6550
Gly Ile Cys Asp Glu  Asn Gly Ala Asn Asp  Phe Met Leu Arg Asp
                2090                 2095                 2100

ggc aca gtc acc aca  gac tgg aaa aca ctt  gtt cag gaa tgg act       6595
Gly Thr Val Thr Thr  Asp Trp Lys Thr Leu  Val Gln Glu Trp Thr
                2105                 2110                 2115

gtg cag cgg cca ggg  cag acg tgc cag ccc  atc ctg gag gag cag       6640
Val Gln Arg Pro Gly  Gln Thr Cys Gln Pro  Ile Leu Glu Glu Gln
                2120                 2125                 2130

tgt ctt gtc ccc gac  agc tcc cac tgc cag  gtc ctc ctc tta cca       6685
Cys Leu Val Pro Asp  Ser Ser His Cys Gln  Val Leu Leu Leu Pro
                2135                 2140                 2145

ctg ttt gct gaa tgc  cac aag gtc ctg gct  cca gcc aca ttc tat       6730
Leu Phe Ala Glu Cys  His Lys Val Leu Ala  Pro Ala Thr Phe Tyr
                2150                 2155                 2160

gcc atc tgc cag cag  gac agt tgc cac cag  gag caa gtg tgt gag       6775
Ala Ile Cys Gln Gln  Asp Ser Cys His Gln  Glu Gln Val Cys Glu
                2165                 2170                 2175

gtg atc gcc tct tat  gcc cac ctc tgt cgg  acc aac ggg gtc tgc       6820
Val Ile Ala Ser Tyr  Ala His Leu Cys Arg  Thr Asn Gly Val Cys
                2180                 2185                 2190

gtt gac tgg agg aca  cct gat ttc tgt gct  atg tca tgc cca cca       6865
Val Asp Trp Arg Thr  Pro Asp Phe Cys Ala  Met Ser Cys Pro Pro
                2195                 2200                 2205

tct ctg gtc tac aac  cac tgt gag cat ggc  tgt ccc cgg cac tgt       6910
Ser Leu Val Tyr Asn  His Cys Glu His Gly  Cys Pro Arg His Cys
                2210                 2215                 2220

gat ggc aac gtg agc  tcc tgt ggg gac cat  ccc tcc gaa ggc tgt       6955
Asp Gly Asn Val Ser  Ser Cys Gly Asp His  Pro Ser Glu Gly Cys
                2225                 2230                 2235

ttc tgc cct cca gat  aaa gtc atg ttg gaa  ggc agc tgt gtc cct       7000
Phe Cys Pro Pro Asp  Lys Val Met Leu Glu  Gly Ser Cys Val Pro
                2240                 2245                 2250

gaa gag gcc tgc act  cag tgc att ggt gag  gat gga gtc cag cac       7045
Glu Glu Ala Cys Thr  Gln Cys Ile Gly Glu  Asp Gly Val Gln His
                2255                 2260                 2265

cag ttc ctg gaa gcc  tgg gtc ccg gac cac  cag ccc tgt cag atc       7090
Gln Phe Leu Glu Ala  Trp Val Pro Asp His  Gln Pro Cys Gln Ile
                2270                 2275                 2280

tgc aca tgc ctc agc  ggg cgg aag gtc aac  tgc aca acg cag ccc       7135
Cys Thr Cys Leu Ser  Gly Arg Lys Val Asn  Cys Thr Thr Gln Pro
                2285                 2290                 2295

tgc ccc acg gcc aaa  gct ccc acg tgt ggc  ctg tgt gaa gta gcc       7180
Cys Pro Thr Ala Lys  Ala Pro Thr Cys Gly  Leu Cys Glu Val Ala
                2300                 2305                 2310

cgc ctc cgc cag aat  gca gac cag tgc tgc  ccc gag tat gag tgt       7225
Arg Leu Arg Gln Asn  Ala Asp Gln Cys Cys  Pro Glu Tyr Glu Cys
```

```
                2315                2320                2325

gtg tgt gac cca gtg  agc tgt gac ctg ccc  cca gtg cct cac tgt       7270
Val Cys Asp Pro Val  Ser Cys Asp Leu Pro  Pro Val Pro His Cys
                2330                2335                2340

gaa cgt ggc ctc cag  ccc aca ctg acc aac  cct ggc gag tgc aga       7315
Glu Arg Gly Leu Gln  Pro Thr Leu Thr Asn  Pro Gly Glu Cys Arg
                2345                2350                2355

ccc aac ttc acc tgc  gcc tgc agg aag gag  gag tgc aaa aga gtg       7360
Pro Asn Phe Thr Cys  Ala Cys Arg Lys Glu  Glu Cys Lys Arg Val
                2360                2365                2370

tcc cca ccc tcc tgc  ccc ccg cac cgt ttg  ccc acc ctt cgg aag       7405
Ser Pro Pro Ser Cys  Pro Pro His Arg Leu  Pro Thr Leu Arg Lys
                2375                2380                2385

acc cag tgc tgt gat  gag tat gag tgt gcc  tgc aac tgt gtc aac       7450
Thr Gln Cys Cys Asp  Glu Tyr Glu Cys Ala  Cys Asn Cys Val Asn
                2390                2395                2400

tcc aca gtg agc tgt  ccc ctt ggg tac ttg  gcc tca act gcc acc       7495
Ser Thr Val Ser Cys  Pro Leu Gly Tyr Leu  Ala Ser Thr Ala Thr
                2405                2410                2415

aat gac tgt ggc tgt  acc aca acc acc tgc  ctt ccc gac aag gtg       7540
Asn Asp Cys Gly Cys  Thr Thr Thr Thr Cys  Leu Pro Asp Lys Val
                2420                2425                2430

tgt gtc cac cga agc  acc atc tac cct gtg  ggc cag ttc tgg gag       7585
Cys Val His Arg Ser  Thr Ile Tyr Pro Val  Gly Gln Phe Trp Glu
                2435                2440                2445

gag ggc tgc gat gtg  tgc acc tgc acc gac  atg gag gat gcc gtg       7630
Glu Gly Cys Asp Val  Cys Thr Cys Thr Asp  Met Glu Asp Ala Val
                2450                2455                2460

atg ggc ctc cgc gtg  gcc cag tgc tcc cag  aag ccc tgt gag gac       7675
Met Gly Leu Arg Val  Ala Gln Cys Ser Gln  Lys Pro Cys Glu Asp
                2465                2470                2475

agc tgt cgg tcg ggc  ttc act tac gtt ctg  cat gaa ggc gag tgc       7720
Ser Cys Arg Ser Gly  Phe Thr Tyr Val Leu  His Glu Gly Glu Cys
                2480                2485                2490

tgt gga agg tgc ctg  cca tct gcc tgt gag  gtg gtg act ggc tca       7765
Cys Gly Arg Cys Leu  Pro Ser Ala Cys Glu  Val Val Thr Gly Ser
                2495                2500                2505

ccg cgg ggg gac tcc  cag tct tcc tgg aag  agt gtc ggc tcc cag       7810
Pro Arg Gly Asp Ser  Gln Ser Ser Trp Lys  Ser Val Gly Ser Gln
                2510                2515                2520

tgg gcc tcc ccg gag  aac ccc tgc ctc atc  aat gag tgt gtc cga       7855
Trp Ala Ser Pro Glu  Asn Pro Cys Leu Ile  Asn Glu Cys Val Arg
                2525                2530                2535

gtg aag gag gag gtc  ttt ata caa caa agg  aac gtc tcc tgc ccc       7900
Val Lys Glu Glu Val  Phe Ile Gln Gln Arg  Asn Val Ser Cys Pro
                2540                2545                2550

cag ctg gag gtc cct  gtc tgc ccc tcg ggc  ttt cag ctg agc tgt       7945
Gln Leu Glu Val Pro  Val Cys Pro Ser Gly  Phe Gln Leu Ser Cys
                2555                2560                2565

aag acc tca gcg tgc  tgc cca agc tgt cgc  tgt gag cgc atg gag       7990
Lys Thr Ser Ala Cys  Cys Pro Ser Cys Arg  Cys Glu Arg Met Glu
                2570                2575                2580

gcc tgc atg ctc aat  ggc act gtc att ggg  ccc ggg aag act gtg       8035
Ala Cys Met Leu Asn  Gly Thr Val Ile Gly  Pro Gly Lys Thr Val
                2585                2590                2595

atg atc gat gtg tgc  acg acc tgc cgc tgc  atg gtg cag gtg ggg       8080
Met Ile Asp Val Cys  Thr Thr Cys Arg Cys  Met Val Gln Val Gly
                2600                2605                2610

gtc atc tct gga ttc  aag ctg gag tgc agg  aag acc acc tgc aac       8125
```

-continued

```
Val Ile Ser Gly Phe  Lys Leu Glu Cys Arg  Lys Thr Thr Cys Asn
                2615                 2620                 2625

ccc tgc ccc ctg ggt  tac aag gaa gaa aat  aac aca ggt gaa tgt      8170
Pro Cys Pro Leu Gly  Tyr Lys Glu Glu Asn  Asn Thr Gly Glu Cys
                2630                 2635                 2640

tgt ggg aga tgt ttg  cct acg gct tgc acc  att cag cta aga gga      8215
Cys Gly Arg Cys Leu  Pro Thr Ala Cys Thr  Ile Gln Leu Arg Gly
                2645                 2650                 2655

gga cag atc atg aca  ctg aag cgt gat gag  acg ctc cag gat ggc      8260
Gly Gln Ile Met Thr  Leu Lys Arg Asp Glu  Thr Leu Gln Asp Gly
                2660                 2665                 2670

tgt gat act cac ttc  tgc aag gtc aat gag  aga gga gag tac ttc      8305
Cys Asp Thr His Phe  Cys Lys Val Asn Glu  Arg Gly Glu Tyr Phe
                2675                 2680                 2685

tgg gag aag agg gtc  aca ggc tgc cca ccc  ttt gat gaa cac aag      8350
Trp Glu Lys Arg Val  Thr Gly Cys Pro Pro  Phe Asp Glu His Lys
                2690                 2695                 2700

tgt ctg gct gag gga  ggt aaa att atg aaa  att cca ggc acc tgc      8395
Cys Leu Ala Glu Gly  Gly Lys Ile Met Lys  Ile Pro Gly Thr Cys
                2705                 2710                 2715

tgt gac aca tgt gag  gag cct gag tgc aac  gac atc act gcc agg      8440
Cys Asp Thr Cys Glu  Glu Pro Glu Cys Asn  Asp Ile Thr Ala Arg
                2720                 2725                 2730

ctg cag tat gtc aag  gtg gga agc tgt aag  tct gaa gta gag gtg      8485
Leu Gln Tyr Val Lys  Val Gly Ser Cys Lys  Ser Glu Val Glu Val
                2735                 2740                 2745

gat atc cac tac tgc  cag ggc aaa tgt gcc  agc aaa gcc atg tac      8530
Asp Ile His Tyr Cys  Gln Gly Lys Cys Ala  Ser Lys Ala Met Tyr
                2750                 2755                 2760

tcc att gac atc aac  gat gtg cag gac cag  tgc tcc tgc tgc tct      8575
Ser Ile Asp Ile Asn  Asp Val Gln Asp Gln  Cys Ser Cys Cys Ser
                2765                 2770                 2775

ccg aca cgg acg gag  ccc atg cag gtg gcc  ctg cac tgc acc aat      8620
Pro Thr Arg Thr Glu  Pro Met Gln Val Ala  Leu His Cys Thr Asn
                2780                 2785                 2790

ggc tct gtt gtg tac  cat gag gtt ctc aat  gcc atg gag tgc aaa      8665
Gly Ser Val Val Tyr  His Glu Val Leu Asn  Ala Met Glu Cys Lys
                2795                 2800                 2805

tgc tcc ccc agg aag  tgc agc aag tgaggctgct gcagctgcat gggtgcctgc  8719
Cys Ser Pro Arg Lys  Cys Ser Lys
                2810

tgctgcctgc cttggcctga tggccaggcc agagtgctgc cagtcctctg catgttctgc  8779

tcttgtgccc ttctgagccc acaataaagg ctgagctctt atcttgcaaa aggc        8833
```

METHODS AND KITS FOR MEASURING VON WILLEBRAND FACTOR

CROSS-REFERENCE TO RELATED APPLICATIONS

This application is a continuation of U.S. patent application Ser. No. 13/669,866, filed Nov. 6, 2012 (now issued as U.S. Pat. No. 8,865,415), which is a continuation of U.S. patent application Ser. No. 13/153,105, filed Jun. 3, 2011 (now issued as U.S. Pat. No. 8,318,444), which is a continuation of U.S. patent application Ser. No. 12/197,057, filed Aug. 22, 2008 (now issued as U.S. Pat. No. 8,163,496), which claims the benefit of U.S. Provisional Patent Application No. 60/957,604, filed Aug. 23, 2007, all of which are incorporated by reference as if set forth in their entirety for all purposes.

STATEMENT REGARDING FEDERALLY SPONSORED RESEARCH

This invention was made with United States government support under RO1-HL033721-19 and RO1-HL081588-03, awarded by the National Institutes of Health. The government has certain rights in this invention.

BACKGROUND

The invention relates generally to methods and kits for measuring von Willebrand factor (VWF), and more particularly to methods and kits for measuring VWF that do not require a platelet aggregation agonist, such as ristocetin.

VWF is a multimeric glycoprotein synthesized by megakaryocytes and endothelial cells, which is subsequently secreted into blood plasma as a spectrum of multimers. VWF binds other proteins, especially proteins involved in hemostasis, such as Factor VIII (an essential clotting factor that participates in the intrinsic pathway of blood coagulation) and platelet glycoprotein Ib (GPIb; a component of a platelet adhesion receptor complex). VWF is deficient or defective in von Willebrand disease (VWD) and is involved in a large number of other diseases, including thrombotic thrombocytopenic purpura, Heyde's syndrome and possibly hemolytic-uremic syndrome. See, Sadler J, "Biochemistry and genetics of von Willebrand factor". Annu Rev. Biochem. 67:395-424 (1998). VWF levels can be affected by many factors including ABO blood group and ethnicity.

VWD is a common bleeding disorder characterized by either qualitative or quantitative defects in tests for VWF. Symptoms of VWD include easy bruising, menorrhagia and epistaxis. Currently, many types of hereditary VWD are known (e.g., type 1; type 2A, 2B, 2M, 2N and type 3, as well as platelet-type, pseudo VWD, which results from a defect in platelet GPIb); however, acquired forms of VWD are also known, but are less frequently observed. Of particular interest herein is platelet-type, pseudo VWD. In contrast to the other forms of VWD, the genetic defect in platelet-type, pseudo VWD is in platelets rather than VWF and is characterized by abnormally high binding affinity of an individual's platelets to VWF, leading to a characteristic platelet hyper-responsiveness in vitro to a low concentration of ristocetin.

Additional screening tests for VWD include those that measure Factor VIII activity, VWF antigen (VWF:Ag), VWF binding to collagen (VWF:CB) and VWF ristocetin cofactor activity (VWF:RCo). Of particular interest herein is VWF:RCo, which is presently the standard for measurement of VWF function. VWF:RCo utilizes an ability of VWF to bind platelet GPIb following activation by ristocetin, which results in a VWF-dependent agglutination of platelets that can be measured quantitatively by platelet aggregometry or turbidometry. See, Macfarlane D, et al., "A method for assaying von Willebrand factor (ristocetin cofactor)," Thromb. Diath. Haemorrh. 34:306-308 (1975). In fact, an international reference standard for VWF:RCo was assigned a biologic activity in international units by the World Health Organization (WHO) and the Scientific and Standardization Committee of the International Society on Thrombosis and Haemostasis (ISTH).

Unfortunately, VWF:RCo, has several shortcomings. For one, VWF:RCo has high intra- and inter-assay imprecision because of its dependence on ristocetin. See, e.g., Chng W, et al., "Differential effect of the ABO blood group on von Willebrand factor collagen binding activity and ristocetin cofactor assay," Blood Coagul. Fibrinolysis 16:75-78 (2005); Favaloro E, "An update on the von Willebrand factor collagen binding assay: 21 years of age and beyond adolescence but not yet a mature adult," Semin. Thromb. Hemost. 33:727-744 (2007); and Riddel A, et al., "Use of the collagen-binding assay for von Willebrand factor in the analysis of type 2M von Willebrand disease: a comparison with the ristocetin cofactor assay," Br. J. Haematol. 116:187-192 (2002). Federici et at recently described an alternative assay with improved reproducibility that used recombinant GPIb in an enzyme-linked immunosorbant assay of VWF binding; however, it is ristocetin dependent. See, Federici A, et al., "A sensitive ristocetin co-factor activity assay with recombinant glycoprotein Ib for diagnosis of patients with low von Willebrand factor levels," Haematologica 89:77-85 (2004).

In addition, VWF:RCo does not always reflect the true in vivo function of VWF when mutations or polymorphisms are in the ristocetin-binding region of VWF. For example, some individuals have VWF mutations that show a reduced interaction with ristocetin such that VWF:RCo is markedly reduced (e.g., <0.12 IU/dL), although they have no bleeding symptoms even with a major surgical challenge. See, Flood V, et al., "Common VWF haplotypes in normal African-Americans and Caucasians recruited into the ZPMCB-VWD and their impact on VWF laboratory testing," Blood 10:Abstract 714 (2007); Mackie I, et al., "Ristocetin-induced platelet agglutination in Afro-Caribbean and Caucasian people," Br. J. Haematol. 50:171-173 (1982); and Miller C, et al., "Measurement of von Willebrand factor activity: relative effects of ABO blood type and race," J. Thromb. Haemost. 1:2191-2197 (2003). These individuals, who appear to have a polymorphism in the ristocetin-binding region, do not have an abnormality in the binding of VWF to platelet GPIb.

Furthermore, VWF:RCo is affected by high-affinity VWF/platelet disorders. For example, individuals with platelet-type, pseudo VWD have GPIb mutations that cause spontaneous binding of their platelets to VWF. See, Franchini M, et al., "Clinical, laboratory and therapeutic aspects of platelet-type von Willebrand disease," Int. J. Lab. Hematol. 30:91-94 (2008); Miller J & Castella A, "Platelet-type von Willebrand's disease: characterization of a new bleeding disorder," Blood 60:790-794 (1982); and Miller J, "Platelet-type von Willebrand's Disease," Thromb. Haemost. 75:865-869 (1996). Likewise, individuals with type 2B VWD have VWF mutations that cause spontaneous binding to platelets. See, Weiss H, "Type 2B von Willebrand disease and related disorders of patients with increased ristocetin-induced platelet aggregation: what they tell us about the role of von Willebrand factor in hemostasis," J. Thromb. Haemost. 2:2055-2056 (2004).

Because of the wide variability and reproducibility of VWF:RCo, the art desires a VWF function assay that does not require a platelet aggregation agonist, such as ristocetin (i.e., ristocetinless).

BRIEF SUMMARY

The invention relates generally to methods and kits for measuring VWF without requiring a platelet agglutination agonist by utilizing recombinant platelet GPIb gain-of-function mutations. As used herein, a "platelet agglutination agonist" means an agent that facilitates adhesion between VWF and GPIb in platelet agglutination tests. Examples of platelet agglutination agonist include, but are not limited to, ristocetin and botrocetin.

In a first aspect, the present invention is summarized as a method of measuring VWF without requiring a platelet agglutination agonist by providing a surface with immobilized recombinant platelet GPIbα having at least two mutations selected from G233V, D235Y and M239V relative to SEQ ID NO:2 or a functional fragment thereof. The method also includes contacting a sample having or suspected of having VWF with the immobilized GPIbα or functional fragment thereof without using the platelet agglutination agonist. The method also includes detecting a complex, if any, of VWF and the immobilized GPIbα or functional fragment thereof.

In some embodiments of the first aspect, the surface can be a cell surface such that the method is a flow cytometry (FC) or fluorescence-activated cell sorting (FACS) assay. Suitable host cells can be a *Xenopus* oocyte, CHO-K1 cell, L929 cell, HEK-293T cell, COS-7 cell or S2 cell engineered to comprise a polynucleotide encoding platelet GPIbα having the at least two mutations selected from the group consisting of G233V, D235Y and M239V relative to SEQ ID NO:2 or a functional fragment thereof. The host cell also can be engineered to further comprise a polynucleotide encoding platelet glycoprotein Ibβ (GPIbβ; SEQ ID NO:4) and/or optionally platelet glycoprotein IX (GP-IX; SEQ ID NO:8) or functional fragments thereof.

In some embodiments of the first aspect, the surface can be a solid-phase surface such that the method is an enzyme-linked immunosorbant assay (ELISA). The solid-phase surface can be agarose, glass, latex or plastic.

In some embodiments of the first aspect, the complex can be detected with a labeled anti-VWF antibody or functional fragment thereof, such as a fluorescently labeled antibody or fluorescently labeled functional fragment thereof. Alternatively, the complex can be detected by surface plasmon resonance or quasi-elastic light scattering.

In some embodiments of the first aspect, the sample can be a biological sample from an individual having or suspected of having VWD, such as plasma.

In some embodiments of the first aspect, the at least two mutations can be D235Y/G233V, D235Y/M239V or G233V/M239V. In other embodiments of the first aspect, the at least two mutation can be a triple mutation, such as D235Y/G233V/M239V.

In a second aspect, the present invention is summarized as a kit for measuring VWF that includes recombinant platelet GPIbα having at least two mutations selected from G233V, D235Y and M239V relative to SEQ ID NO:2 or a functional fragment thereof. The kit also includes a reagent to detect a complex of VWF and GPIbα.

In some embodiments of the second aspect, the reagent can be a labeled anti-VWF antibody or labeled functional fragment thereof, such as a fluorescently labeled antibody or fluorescently labeled functional fragment thereof.

In some embodiments of the second aspect, the kit further includes a negative or positive control or both. If included, the negative control can be VWF-depleted plasma. If included, the positive control can be pooled plasma from individuals that do not have VWD or can be a commercially available standard, such as those available from WHO and ISTH. In other embodiments of the second aspect, the kit further includes an abnormal control. If included, the abnormal control can be pooled plasma from individuals with variant forms of VWD, such as type-2A, 2B or 2M VWD, as well as pooled plasma from individuals with true loss of in vivo VWF function or pooled plasma individuals that are not appropriately assayed using VWF:RCo (i.e., plasma from individuals having any gain-of-function mutation in VWF).

In some embodiments of the second aspect, the at least two mutations can be selected from D235Y/G233V, D235Y/M239V or G233V/M239V. In other embodiments of the second aspect, the at least two mutations can be a triple mutation, such as D235Y/G233V/M239V.

In some embodiments of the second aspect, the recombinant platelet GPIbα having at least two mutations selected from G233V, D235Y and M239V relative to SEQ ID NO:2 or functional fragment thereof can be immobilized to a surface. In certain embodiments, the surface can be a host cell surface of a host cell that does not natively express platelet GPIbα, as described above. In certain other embodiments, the surface can be a solid-phase surface, as described above.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

Figure 1:
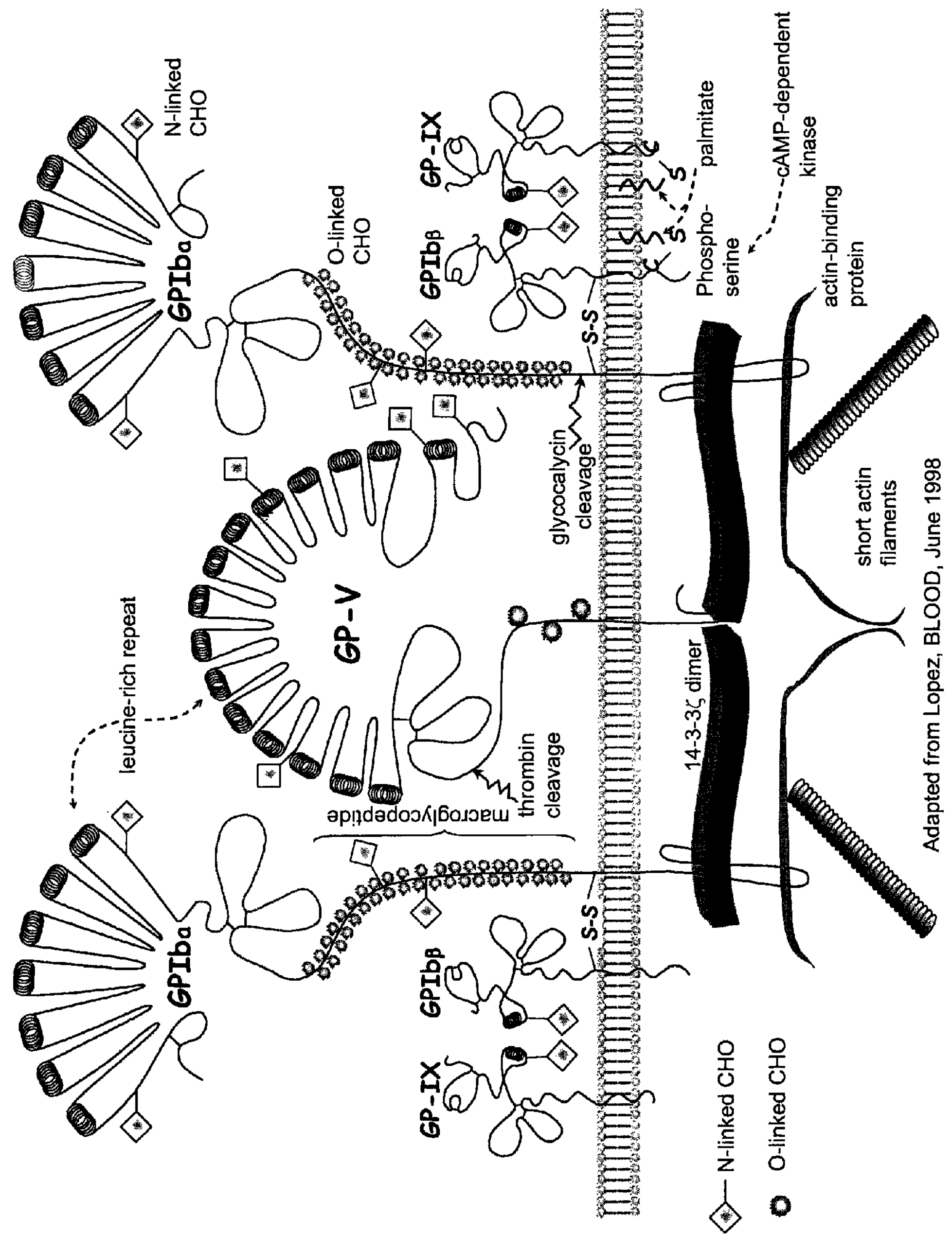
FIG. 1 is a schematic illustration of the platelet adhesion receptor, which shows the components of the receptor, including GPIbα, GPIbβ, GP-V and GP-IX.

While the present invention is susceptible to various modifications and alternative forms, exemplary embodiments thereof are shown by way of example in the drawings and are herein described in detail. It should be understood, however, that the description of preferred embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF PREFERRED EMBODIMENTS

The present invention stems from the inventor's observation that some individuals with VWD have VWF mutations that lower VWF:RCo (i.e., <10 IU/dL), even though their in vivo VWF function is normal (i.e., VWF still binds to the platelet adhesion receptor component GPIb). See, Friedman K, et al., "Factitious diagnosis of type 2M von Willebrand disease (VWD) with a mutation in von Willebrand factor (VWF) that affects the ristocetin cofactor assay but does not significantly affect VWF function in vitro," Blood 98:536a (2001).

In contrast, other individuals with VWD (i.e., type 2B and platelet-type VWD) have VWF or GPIbα mutations that lower the concentration of ristocetin required for platelet aggregation in an assay for VWF function. This paradox results from gain-of-function mutations that cause VWF multimers and the GPIb receptors on platelets to bind more tightly to one another. The inventor hypothesized that recombinant gain-of-function GPIbα mutations could be useful in assays for VWF function, thereby avoiding ristocetin (i.e., ristocetinless). As used herein, "ristocetinless" or "agonistless" means that ristocetin or other platelet agglutination agonists (i.e., botrocetin) are not required in a VWF assay.

The present invention therefore broadly relates to novel methods and kits for VWF utilizing gain-of-function GPIbα mutations, especially GPIbα mutations identified in individuals having platelet-type, pseudo VWD, to measure VWF (herein called "VWF:IbCo"). The methods and kits are useful in a variety of applications. For example, the methods and kits disclosed herein may be used for diagnosing VWD in an individual suspected of having VWD, classifying VWD in an individual diagnosed with VWD and monitoring treatment in an individual having VWD.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

As used herein, "about" means within 5% of a stated concentration range, purity range, temperature range or stated time frame.

As used herein, a "coding sequence" means a sequence that encodes a particular polypeptide, such as GPIbα, and is a nucleic acid sequence that is transcribed (in the case of DNA) and translated (in the case of mRNA) into that polypeptide in vitro or in vivo when placed under the control of appropriate regulatory sequences. The boundaries of the coding sequence are determined by a start codon at a 5' (amino) terminus and a translation stop codon at a 3' (carboxy) terminus. A coding sequence can include, but is not limited to, viral nucleic acid sequences, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

As used herein, an "expression sequence" means a control sequence operably linked to a coding sequence.

As used herein, "control sequences" means promoter sequences, polyadenylation signals, transcription termination sequences, upstream regulatory domains, origins of replication, internal ribosome entry sites ("IRES"), enhancers, and the like, which collectively provide for replication, transcription and translation of a coding sequence in a recipient cell. Not all of these control sequences need always be present so long as the selected coding sequence is capable of being replicated, transcribed and translated in an appropriate host cell.

As used herein, a "promoter" means a nucleotide region comprising a nucleic acid (i.e., DNA) regulatory sequence, wherein the regulatory sequence is derived from a gene that is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is repressed by an analyte, cofactor, regulatory protein, etc.) and "constitutive promoters" (where expression of a polynucleotide sequence operably linked to the promoter is unregulated and therefore continuous).

As used herein, a "nucleic acid" sequence means a DNA or RNA sequence. The term encompasses sequences that include, but are not limited to, any of the known base analogues of DNA and RNA such as 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine and 2,6-diaminopurine.

As used herein, "operably linked" means that elements of an expression sequence are configured so as to perform their usual function. Thus, control sequences (i.e., promoters) operably linked to a coding sequence are capable of effecting expression of the coding sequence. The control sequences need not be contiguous with the coding sequence, so long as they function to direct the expression thereof. For example, intervening untranslated, yet transcribed, sequences can be present between a promoter and a coding sequence, and the promoter sequence can still be considered "operably linked" to the coding sequence.

As used herein, "operable interaction" means that subunits of a polypeptide (e.g., the components of the platelet adhesion receptor, such as GPIbβ and/or GP-IX), and any other accessory proteins, that are heterologously expressed in a host cell assemble into a functioning platelet adhesion receptor (i.e., capable of binding with VWF or functional fragments thereof capable of binding VWF).

As used herein, a "vector" means a replicon, such as a plasmid, phage or cosmid, to which another nucleic acid segment may be attached so as to bring about the replication of the attached segment. A vector is capable of transferring gene sequences to target cells (e.g., bacterial plasmid vectors, particulate carriers and liposomes).

Typically, the terms "vector construct," "expression vector," "gene expression vector," "gene delivery vector," "gene transfer vector" and "expression cassette" all refer to an assembly that is capable of directing the expression of a coding sequence or gene of interest. Thus, the terms include cloning and expression vehicles.

As used herein, an "isolated polynucleotide" or "isolated polypeptide" means a polynucleotide or polypeptide isolated from its natural environment or prepared using synthetic methods such as those known to one of ordinary skill in the art. Complete purification is not required in either case. The polynucleotides and polypeptides described herein can be isolated and purified from normally associated material in conventional ways, such that in the purified preparation the polynucleotide or polypeptide is the predominant species in the preparation. At the very least, the degree of purification is such that extraneous material in the preparation does not interfere with use of the polynucleotide or polypeptide in the manner disclosed herein. The polynucleotide or polypeptide is at least about 85% pure; alternatively, at least about 95% pure; and alternatively, at least about 99% pure.

Further, an isolated polynucleotide has a structure that is not identical to that of any naturally occurring nucleic acid molecule or to that of any fragment of a naturally occurring genomic nucleic acid spanning more than one gene. An isolated polynucleotide also includes, without limitation, (a) a nucleic acid having a sequence of a naturally occurring genomic or extrachromosomal nucleic acid molecule, but which is not flanked by the coding sequences that flank the sequence in its natural position; (b) a nucleic acid incorporated into a vector or into a prokaryote or eukaryote host cell's genome such that the resulting polynucleotide is not identical to any naturally occurring vector or genomic DNA; (c) a separate molecule such as a cDNA, a genomic fragment, a fragment produced by polymerase chain reaction (PCR) or a restriction fragment; and (d) a recombinant nucleotide sequence that is part of a hybrid gene (i.e., a gene encoding a fusion protein). Specifically excluded from this definition are nucleic acids present in mixtures of clones, e.g., as these occur in a DNA library such as a cDNA or genomic DNA library. An isolated polynucleotide can be modified or unmodified DNA or RNA, whether fully or partially single-stranded or double-stranded or even triple-stranded. In addition, an isolated polynucleotide can be chemically or enzymatically modified and can include so-called non-standard bases such as inosine.

As used herein, "homologous" means those polynucleotides or polypeptides sharing at least about 90% or at least about 95% sequence identity to, e.g., SEQ ID NOS:1-6, respectively, that result in functional polypeptides that bind VWF. For example, a polypeptide that is at least about 90% or at least about 95% identical to the GPIbα mutations discussed herein is expected to be a constituent of the platelet adhesion receptor. One of ordinary skill in the art understands that modifications to either the polynucleotide or the polypeptide includes substitutions, insertions (e.g., adding no more than about ten nucleotides or amino acids) and deletions (e.g., deleting no more than about ten nucleotides or amino acids). These modifications can be introduced into the polynucleotide or polypeptide described below without abolishing structure and ultimately, function. Polynucleotides and/or polypeptides containing such modifications can be used in the methods of the present invention. Such polypeptides can be identified by using the screening methods described below.

An isolated nucleic acid containing a polynucleotide (or its complement) that can hybridize to any of the uninterrupted nucleic acid sequences described above, under either stringent or moderately stringent hybridization conditions, is also within the scope of the present invention. Stringent hybridization conditions are defined as hybridizing at 68° C. in 5×SSC/5× Denhardt's solution/1.0% SDS, and washing in 0.2×SSC/0.1% SDS+/−100 μg/ml denatured salmon sperm DNA at room temperature, and moderately stringent hybridization conditions are defined as washing in the same buffer at 42° C. Additional guidance regarding such conditions is readily available in the art, e.g., in Sambrook J, et al. (eds.), "Molecular cloning: a laboratory manual," (3rd ed. Cold Spring Harbor Press, Cold Spring Harbor, N.Y. 2001); and Ausubel F, et al. (eds.), "Current Protocols in Molecular Biology," (John Wiley & Sons, N.Y. 1995), each of which is incorporated herein by reference as if set forth in its entirety.

It is well known in the art that amino acids within the same conservative group can typically substitute for one another without substantially affecting the function of a protein. For the purpose of the present invention, such conservative groups are set forth in Table 1 and are based on shared properties.

TABLE 1

Amino Acid Conservative Substitutions.

| Original Residue | Conservative Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |

TABLE 1-continued

Amino Acid Conservative Substitutions.

| Original Residue | Conservative Substitution |
|---|---|
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

As used herein, an "antibody" means a monoclonal and polyclonal antibody and can belong to any antibody class (i.e., IgG, IgM, IgA, etc.). One of ordinary skill in the art is familiar with methods for making monoclonal antibodies (Mab). For example, one of ordinary skill in the art can make monoclonal antibodies by isolating lymphocytes and fusing them with myeloma cells, thereby producing hybridomas. See, e.g., Milstein C, "Handbook of experimental immunology," (Blackwell Scientific Pub., 1986); and Goding J, "Monoclonal antibodies: principles and practice," (Academic Press, 1983), each of which is incorporated herein by reference as if set forth in its entirety. The cloned hybridomas are then screened for production of, e.g., "anti-GPIbα" (i.e., antibodies that bind preferentially to GPIbα or fragments thereof) or "anti-VWF" antibodies (i.e., antibodies that bind preferentially to VWF or fragments thereof). Monoclonal antibodies are thus not limited by the manner in which the antibodies are produced, whether such production is in situ or not. Alternatively, antibodies can be produced by recombinant DNA technology including, but not limited, to expression in bacteria, yeast, insect cell lines or mammalian cell lines.

Likewise, one of ordinary skill in the art is familiar with methods of making polyclonal antibodies. For example, one of ordinary skill in the art can make polyclonal antibodies by immunizing a suitable host animal, e.g., such as a rabbit, with an immunogen and using properly diluted serum or isolating immunoglobulins from the serum. The animal may therefore be inoculated with the immunogen, with blood subsequently being removed from the animal and an IgG fraction purified. Other suitable host animals include a chicken, goat, sheep, guinea pig, rat or mouse. If desired, the immunogen may be administered as a conjugate in which the immunogen is coupled, e.g., via a side chain of one of its amino acid residues, to a suitable carrier. The carrier molecule is typically a physiologically acceptable carrier. The antibody obtained may be purified to a purity of up to about 70%, up to about 80%, up to about 90%, up to about 95%, up to about 99% or up to about 100%.

Antibody also encompasses functional fragments, like Fab and F(ab') 2, of anti-GPIbα or anti-VWF antibodies. Treatment of antibodies with proteolytic enzymes, such as papain and pepsin, generates these antibody fragments, especially anti-GPIbα fragments.

Antibodies are typically conjugated to a detectable label for easy visualization. Examples of suitable labels for the methods and kits described herein include, but are not limited to, radiolabels, biotin (which may be detected by avidin or streptavidin conjugated to peroxidase), lanthanides, alkaline phosphatase and fluorescent labels (e.g., fluorescein, rhodamine, especially the Alexa Fluor® family of fluorescent dyes available from Invitrogen/Molecular Probes). Labelling of the antibody can be carried out by, e.g. labeling free amine groups (covalently or non-covalently). Some labels can be detected by using a labeled counter suitable for the detection of the label in question.

Commercially available anti-GPIbα antibodies and anti-VWF antibodies are suitable for use with the methods and kits described herein, and can be obtained from Blood Research Institute (Milwaukee, Wis.) and Dako (Carpinteria, Calif.), respectively.

As shown in FIG. 1, the platelet adhesion receptor is comprised of a combination of four proteins, including GPIb, which is a heterodimer of an alpha chain (GPIbα; GenBank Accession No. NM_000173.4; SEQ ID NOS:1-2) and a beta chain (GPIbβ; GenBank Accession No. NM_000407.4; SEQ ID NOS:3-4) linked by disulfide bonds. Other components of the receptor include GP-V (GenBank Accession No. NM_004488.2; SEQ ID NOS:5-6) and GP-IX (GenBank Accession No. NM_000174.2; SEQ ID NOS:7-8). The platelet adhesion receptor binds to VWF (GenBank Accession No. NM_000552.3; SEQ ID NOS:9-10) to regulate hemostasis and thrombosis.

Of particular interest herein is human GPIbα modified so that a platelet aggregation agonist is not required in assays of VWF function. For example, GPIbα can be modified to include the gain-of-function mutations that cause platelet-type, pseudo VWD including, but not limited to, G233V (see, Miller J, et al., "Mutation in the gene encoding the alpha chain of platelet glycoprotein Ib in platelet-type von Willebrand disease," Proc. Natl. Acad. Sci. USA 88:4761-4765 (1991), incorporated herein by reference as if set forth in its entirety); D235V (see, Dong J, et al., "Novel gain-of-function mutations of platelet glycoprotein IBα by valine mutagenesis in the Cys209-Cys248 disulfide loop, which interacts with the A1 domain of VWF. Functional analysis under static and dynamic conditions," J. Biol. Chem. 275: 27663-27670 (2000), incorporated herein by reference as if set forth in its entirety); M239V (see, Russell S & Roth G, "Pseudo-von Willebrand disease: a mutation in the platelet glycoprotein Ib alpha gene associated with a hyperactive surface receptor," Blood 81:1787-1791(1993), incorporated herein by reference as if set forth in its entirety); G233S (Matsubara Y, et al., "Identification of a novel point mutation in platelet glycoprotein Ib, Gly to Ser at residue 233, in a Japanese family with platelet-type von Willebrand disease," J. Thromb. Haemost. 1:2198-2205 (2003)); and K237V (see, Dong et al., supra). Advantageously, the mutation(s) can be in the $Cys^{209}$-$Cys^{248}$ disulfide loop of GPIbα that compromise hemostasis by increasing the affinity of GPIb for VWF. For example, and as shown below, the inventor found that D235Y is another gain-of-function mutation suitable for use with the methods and kits described herein.

As used herein, a "functional fragment" means a fragment of a component of a platelet adhesion receptor, such as a fragment of GPIbα, having at least two of the previously mentioned mutation, yet retaining its ability to interact with VWF or other substrates. For example, the amino terminus of GPIbα retains its ability to interact with VWF. As shown below, fragments of GPIbα as small as 290 amino acids and having two mutations retained an ability to interact with VWF, although smaller fragments are contemplated. With respect to VWF, a functional fragment may comprise at least the A1 domain, which is the GPIb binding domain. With respect to antibodies, functional fragments are those portions of an antibody that bind to a particular epitope, such as the domains indicated above.

As used herein, a "sample" means a biological sample, such as amniotic fluid, aqueous humor, cerebrospinal fluid, interstitial fluid, lymph, plasma, pleural fluid, saliva, serum, sputum, synovial fluid, sweat, tears, urine, breast milk or tissue that has or is suspected of having VWF. With respect to measuring VWF, plasma is a suitable sample.

As used herein, a "surface" means, e.g., a cell surface or solid-phase surface, such as an unsoluble polymer material, which can be an organic polymer, such as polyamide or a vinyl polymer (e.g., poly(meth)acrylate, polystyrene and polyvinyl alcohol or derivates thereof), a natural polymer, such as cellulose, dextrane, agarose, chitin and polyamino acids, or an inorganic polymer, such as glass or plastic. The solid-phase surface can be in the form of a bead, microcarrier, particle, membrane, strip, paper, film, pearl or plate, particularly a microtiter plate.

One aspect of the present invention includes a diagnostic assay for measuring VWF. The underlying methodology of the assay can be FC, FACS or ELISA, each of which is well known to one of ordinary skill in the art. See, e.g., Alice Giva, "Flow cytometry: first principles," (2nd ed. Wiley-Liss, New York, 2001); Howard Shapiro, "Practical flow cytometry," (4th Ed. Wiley-Liss, New York, 2003); Larry Sklar, "Flow cytometry for biotechnology," (Oxford University Press, New York, 2005); J. Paul Robinson, et al., "Handbook of flow cytometry," (Wiley-Liss, New York, 1993); "Flow cytometry in clinical diagnosis," (3rd ed., Carey, McCoy and Keren, eds., ASCP Press 2001); Lequin R, "Enzyme immunoassay (EIA)/enzyme-linked immunosorbent assay (ELISA)," Clin. Chem. 51:2415-2418 (2005); Wide L & Porath J, "Radioimmunoassay of proteins with the use of Sephadex-coupled antibodies," Biochem. Biophys. Acta. 30:257-260 (1966); Engvall E & Perlman P, "Enzyme-linked immunosorbent assay (ELISA). Quantitative assay of immunoglobulin G," Immunochemistry 8:871-874 (1971); and Van Weemen B & Schuurs A, "Immunoassay using antigen-enzyme conjugates," FEBS Letters 15:232-236 (1971), each of which is incorporated herein by reference as if set forth in its entirety.

As noted above, the surface for the methods and kits described herein can be a host cell surface expressing at least platelet GPIbα for use in FACS. For example, one can heterologously express (either transiently or stably) mutant GPIbα or other components of platelet adhesion receptor (i.e., GPIbβ and/or GP-IX) in host cells. Methods of expressing polynucleotides and their encoded platelet glycoprotein receptor polypeptides in heterologous host cells are known to one of ordinary skill in the art. See, e.g., Tait A, et al., "Phenotype changes resulting in high-affinity binding of von Willebrand factor to recombinant glycoprotein Ib-IX: analysis of the platelet-type von Willebrand disease mutations," Blood 98:1812-1818 (2001), incorporated herein by reference as if set forth in its entirety; and Dong et al., supra.

Cells suitable for use herein preferably do not natively display GPIbα or the other components of the platelet adhesion receptor complex. One such cell type is HEK-293T cells (American Type Culture Collection (ATCC); Manassas, Va.; Catalog No. CRL-11268). See also, Graham F, et al., "Characteristics of a human cell line transformed by DNA from human adenovirus type 5," J. Gen. Virol. 36:59-74 (1977), incorporated herein by reference as if set forth in its entirety. HEK-293 cells are easy to reproduce and to maintain, are amenable to transfection using a wide variety of methods, have a high efficiency of transfection and protein production, have faithful translation and processing of proteins and have a small cell size with minimal processes appropriate for electrophysiological experiments.

Another suitable cell type is COS-7 cells (ATCC; Catalog No. CRL-1651). See also, Gluzman Y, "SV40-transformed simian cells support the replication of early SV40 mutants," Cell 23:175-182 (1981), incorporated herein by reference as if set forth in its entirety. Like HEK-293 cells, COS-7 cells are easy to reproduce and maintain and are amenable to transfection using a wide variety of methods.

Yet another suitable cell type is *Xenopus* oocytes. *Xenopus* oocytes are commonly used for heterologous gene expression because of their large size (~1.0 mm), which makes their handling and manipulation easy. *Xenopus* oocytes are readily amenable to injection, and thus express functional proteins when injected with cRNA for an desired protein.

Yet another suitable cell type is S2 *Drosophila melanogaster* cells. S2 cells are ideal for difficult-to-express proteins, and a S2 expression system is commercially available from Invitrogen (Carlsbad, Calif.). The S2 expression system can be engineered to preferably lack the Bip secretion sequence so that the encoded proteins are expressed on the cell surface. Expression of platelet adhesion receptor components in S2 cells was previously shown by Celikel et al. See, Celikel R, et al., "Modulation of alpha-thrombin function by distinct interactions with platelet glycoprotein Ibα," Science 301:218-221 (2003), incorporated herein by reference as if set forth in its entirety.

Any of the contemplated polynucleotides for the platelet adhesion receptor can be cloned into an expression vector (or plurality of expression vectors) engineered to support expression from the polynucleotides. Suitable expression vectors comprise a transcriptional promoter active in a recipient host cell upstream of, e.g., a GPIbα polynucleotide engineered to have the previously mentioned mutations or additional polynucleotides and can optionally comprise a polyA-addition sequence downstream of the polynucleotide.

The vector(s) can be introduced (or co-introduced) by, for example, transfection or lipofection, into recipient host cells competent to receive and express mutant GPIbα and optionally other components of the platelet adhesion receptor. A commercially available lipofection kit, such as a kit available from Mims Corporation (Madison, Wis.) can be employed. Preferably, the recipient host cells do not natively contain GPIbα, so that the presence of it is completely attributable to expression from the introduced expression vector. Suitable recipient host cells are described above and can express the polypeptides on their surface or secrete them.

Alternatively, the surface for the methods and kits described herein can be a solid-phase surface having platelet GPIbα immobilized thereupon by, e.g., covalent attachment or antibodies. Suitable solid-phase surfaces include the solid-phase surfaces described above. One of ordinary skill in the art is familiar with methods for attaching anti-GPIbα antibodies or functional fragments thereof to solid-phase surfaces. For example, the antibody or functional fragment thereof can be immobilized on the surface directly by covalent coupling or via a carrier such as a linker molecule or an antibody immobilized on the solid-phase surface. The antibody can be a polyclonal or monoclonal antibody, such as anti-GPIbα or a functional fragment thereof. Alternatively, the antibody can be an anti-epitope antibody that recognizes an epitope-tag (e.g., biotin, digoxigenin, GST, hexahistidine, hemagglutinin, FLAG™, c-Myc, VSV-G, V5 and HSV) complexed with GPIbα. Commercially available epitope tags and their respective antibodies are suitable for use with the methods and kits described herein, and can be obtained from Sigma Aldrich (St. Louis, Mo.) and Abcam, Inc. (Cambridge, Mass.).

The methods and kits described herein are thus sensitive to the measurement of the more functional, large VWF multimers, correlates with VWF:Ag in individuals with reduced VWF function, and remains unaffected by mutations that affect VWF binding of ristocetin but do not have a bleeding phenotype.

The invention will be more fully understood upon consideration of the following non-limiting Examples.

EXAMPLES

Example 1

Cells Heterologously Expressing Mutant GPIbα Spontaneous Binding in the Absence Ristocetin Methods: A heterologous platelet adhesion receptor expression system was constructed by transiently transfecting HEK-293T cells (ATCC) with a full-length GPIbα construct encoding a single mutation (i.e., G233V, D235Y or M239V), a double mutation (i.e., G233V/M239V, G233V/D235Y or D235Y/M239V) a triple mutation (i.e., G233V/D235Y/M239V) relative to SEQ ID NO:2 or wild-type GPIbα (SEQ ID NO:2). Some HEK-293T cells also were transiently transfected with GPIbβ and GP-IX constructs encoding SEQ ID NOS:4 and 8, respectively. A mock group of HEK-293T cells were treated similarly, but were transfected with an expression vector lacking the above constructs, thereby serving as controls.

The constructs were cloned in to a pCI-neo vector (Promega; Madison, Wis.) and expressed in HEK-293T cells as described below. In some instances, separate constructs were made for each GPIbα mutation; however, in other instances, a single construct was made having multiple GPIbα mutations.

Briefly, HEK-293T cells were first seeded until they were 50-80% confluent (i.e., 3.5-4×$10^6$/100 mm dish). Typically, the cells were seeded the day before transfection. For transfection, Hanks Balanced Salt Solution (HBSS) and OptiMEM (Invitrogen) were warmed to 37° C. 800 μl of OptiMEM was added to 17×100 polystyrene tubes (2 tubes/plate to be transfected). The following was added to one set of tubes: 4.5 μg of DNA (1.5 μg of each construct) and 20 μl PLUS Reagent (Invitrogen). The following was added to another set of tubes: 30 μl Lipofectamine (Invitrogen). Each set was allowed to incubate at room temperature for 15 minutes. The DNA mixture was then added to the Lipofectamine mixture and incubated at room temperature for 15 minutes. During incubation, the cells were washed twice with 5 ml HBSS. 3.4 ml of OptiMEM was added to the DNA/Lipofectamine mixture, and then added to the HEK-293T cells (total volume=5 ml). The cells were then incubated at 37° C. with 5% $CO_2$ for 3-3.5 hours.

Following transfection, the transfection medium was removed and 8 ml of fresh complete medium was added to the cells. The cells were then incubated at 37° C. with 5% $CO_2$ for about 60 hours. Cells were then harvested for use in a standard FACS assay using ristocetin.

For FACS, about 50 μl of a 1:10 dilution of platelet poor plasma (PPP; source of VWF) in assay buffer was added to the plate and serially diluted 1:2 to final dilution of 1:80. ISTH Lot #3 (GTI; Milwaukee, Wis.) was used as a standard and diluted 1:10 in assay buffer and serially diluted 1:2 to a final dilution of 1:320. The plate was then incubated for one hour at room temperature. After the one-hour incubation, the plate was centrifuged again at 1200 rpm for 5 minutes and the supernatant was discarded.

In some experiments, the PPP was diluted in PBS containing 1% BSA and either 1 mg/ml Ristocetin A (American Biochemical & Pharmaceuticals, Ltd.; Marlton, N.J.) or 1 mg/ml Botrocetin (Sigma Aldrich).

Fluorescently labeled antibodies (anti-GPIbα; Blood Research Institute) were diluted to a final concentration of 5 μg/ml in assay buffer. Fluorescently labeled anti-VWF polyclonal was also was diluted to a final concentration of 5 μg/ml in assay buffer and added to transfected cells incubated in PPP. Normal rabbit IgG (NRIgG; Pierce) and AP-1 were added at a concentration of 5 μg/ml to transfected cells as negative and positive controls, respectively. The plate was then incubated in the dark for one hour at room temperature. Assay buffer was added to each well to bring the final volume to 150 μl, and FACS was performed using a BD LSRII System (Becton Dickinson). Results are shown in VWF:IbCo units.

Figure 2A:
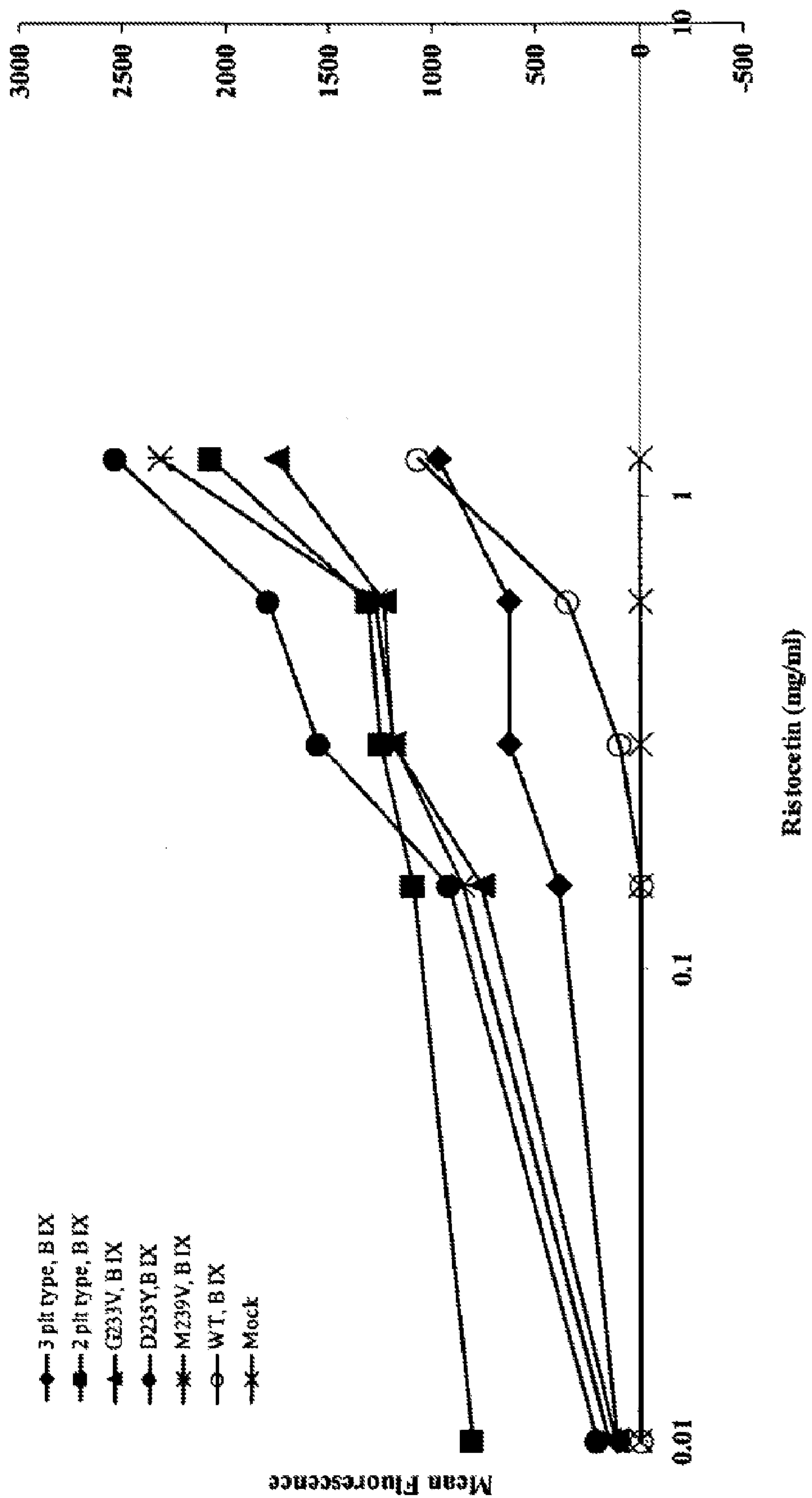
FIG. 2A shows the effect GPIbα mutations (single, double or triple). Y-axis is mean fluorescence and x-axis is log ristocetin concentration in mg/ml), ristocetin.
Figure 2B:
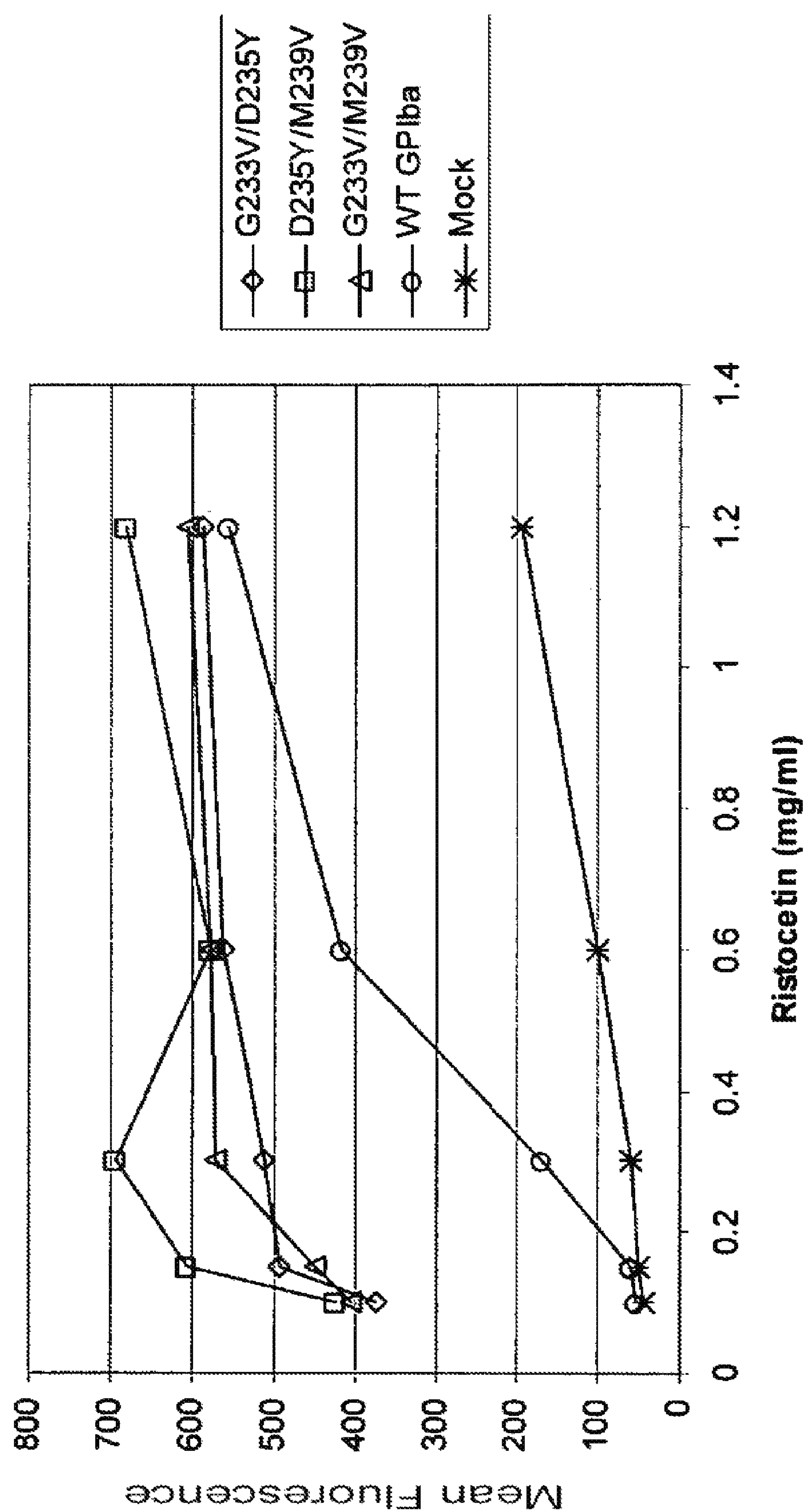
FIG. 2B shows the effect GPIbα mutations (single, double or triple). Y-axis is mean fluorescence and x-axis is log ristocetin concentration in mg/ml) and botrocetin.
Figure 2C:
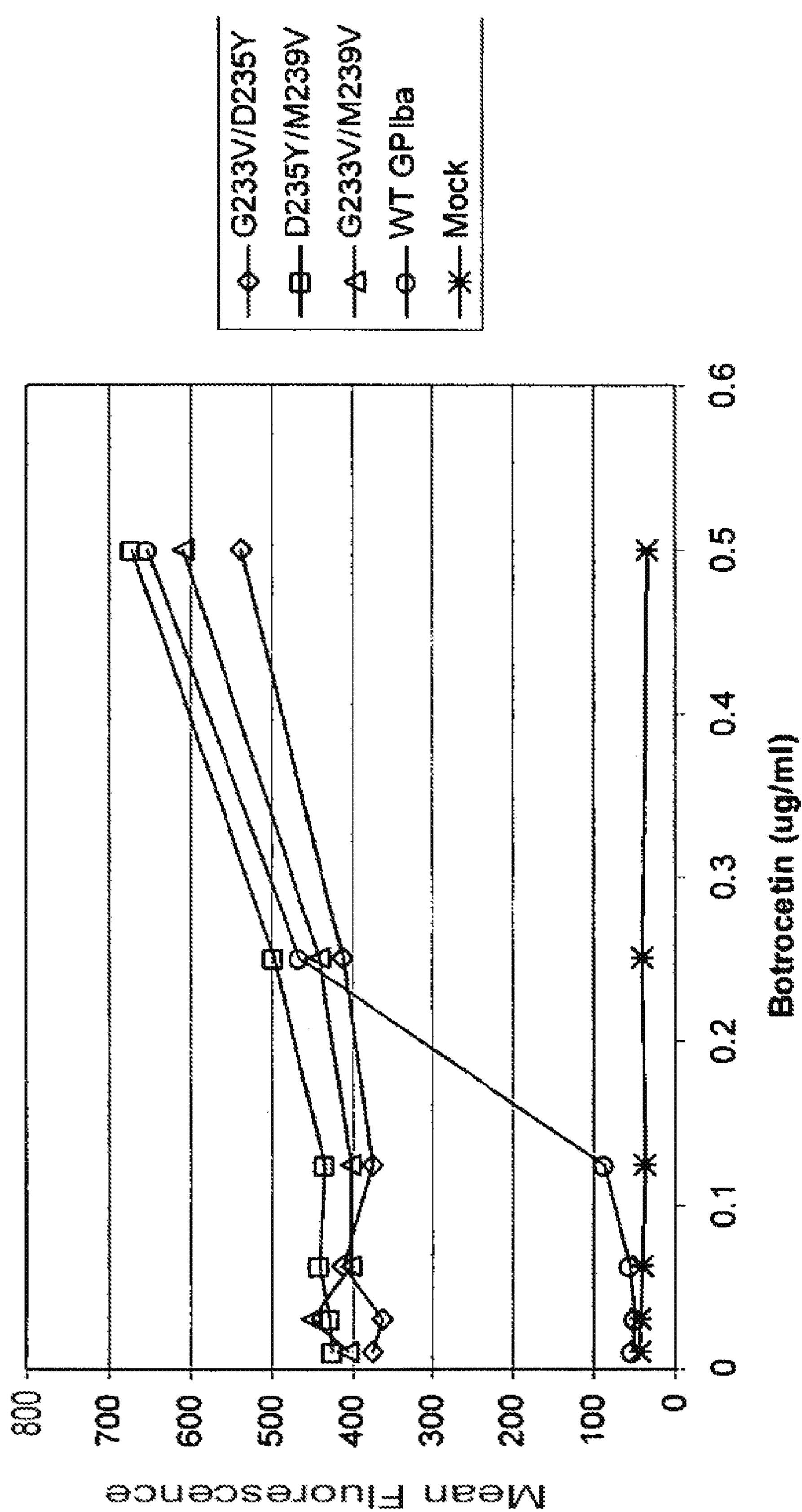
FIG. 2C shows the effect GPIbα mutations (single, double or triple). Y-axis is mean fluorescence and x-axis is log botrocetin concentration in mg/ml) during FACS. Mock is a HEK-293T cells transfected with an empty expression vector.

Results: As shown in FIG. 2A, mock transfected HEK-293T cells did not show any binding in the presence of ristocetin, while cells expressing wild-type GPIbα showed a concentration-dependent decrease in ristocetin binding after 1.2 mg/ml. HEK-293T cells expressing only one of the GPIbα mutations showed increased sensitivity even at low concentrations of ristocetin, which suggests that the binding is independent of ristocetin. Cells expressing two GPIbα mutations showed an extreme sensitivity to ristocetin or alternatively, an increased spontaneous binding that was independent of ristocetin. HEK-293T cells expressing the triple GPIbα mutation (i.e., G233V/D235Y/M239V), however, did not show increased sensitivity/spontaneous binding relative to the double mutants. As shown in FIG. 2B, each of the double mutants (i.e., G233V/M239V, G233V/D235Y or D235Y/M239V) showed comparable spontaneous binding relative to one another that was not significantly affected by ristocetin (i.e., ristocetinless). As expected the, wild-type control showed concentration-dependent increases in VWF:IbCo to ristocetin. As shown in FIG. 2C, VWF:IbCo is not affected by the type of platelet aggregation agonist, as none of the double mutants was significantly affected by botrocetin (i.e., botrocetinless). As expected, wild-type control showed concentration-dependent increases in VWF:IbCo to botrocetin.

Example 2

VWF Function in Patient Samples Using Mutant GPIbα in FACS

Methods: HEK293T cells were transiently transfected with a wild-type GPIbα construct or GPIbα encoding one of the double mutants, as described above. The cells were additionally transfected with the GPIbβ and GP-IX constructs. A group of HEK-293T cells were mock transfected, as describe above.

After forty-eight hours, the transfected cells were lifted from the plate with 3 mM EDTA, resuspended in assay buffer (i.e., 1× PBS containing 2% BSA) and counted. Trypsin was not used, as it potentially can cleave GPIbα from the cell surface. After counting, 1.75×$10^5$ cells were plated 96-well plate (Becton Dickinson; Franklin Lakes, N.J.) as a way of standardizing GPIbα on the plate surface, and the plate was then centrifuged at 2000 rpm for 5 minutes to pellet the cells. The supernatant was discarded.

HEK-293T cells expressing the GPIbα mutations were used in flow cytometry assays to test VWF binding, which was measured with a fluorescently labeled anti-VWF polyclonal antibody from Dako. A normal curve was developed using serial dilutions of reference plasma previously standardized against both the ISTH and WHO VWF standards based on the VWF:Ag international standard that is also standardized for VWF:RCo.

In one set of experiments, normal patient samples were used to determine whether the HEK-293T cells required all components of the platelet adhesion receptor or simply GPIbα. Normal patient samples were used. In another set of experiments, patient samples from normal individuals and individuals having VWD were used in the FACS assay as described above in Example 2.

Samples included 41 normals, 16 type-2M VWD, 5 type-2B VWD and 5 type-2A VWD plasma, Included therein were individuals with apparent type-2M VWD, but without clinical symptoms, and African Americans with a reduced VWF:RCo/VWF:Ag (RCo/Ag) ratio. Of the 16 type-2M VWD samples, 7 had markedly reduced VWF:IbCo (consistent with the VWF:RCo assay), and 9 had normal VWF:IbCo. African Americans with SNPs associated with reduced RCo/Ag ratios had VWF:IbCo assays that correlated with their VWF:Ag in contrast to the abnormal RCo/Ag ratios identified by standard assays. Type-2A individuals exhibited reduced VWF:IbCo assays and multimer size seemed to correlate with VWF:IbCo activity. Thus, measurement of VWF function using the VWF:IbCo assay more directly correlates with VWF function and avoids some of the pitfalls and functional variability of VWF:RCo assays.

Results: As shown in Table 2, GPIbβ and GP-IX are not required for surface expression of the mutant GPIbα, as FACS results from HEK-293T cells expressing multiple components of the plate adhesion receptor were not significantly different from cells expressing only GPIbα.

TABLE 2

Effect of GPIbα Having a Double Mutation With or Without the Other Platelet Adhesion Receptor Components in a FACS.

| Sample | Known VWF:RCo (IU/dL) | GPIbα (G233V/ M239V), GPIbβ and IX | GPIbα | % Diff btw Trans-fec-tions | % Diff. btw GPIbα, GPIbβ and IX & Known | % Diff. btw GPIbα & Known |
|---|---|---|---|---|---|---|
| ISTH 2 | 71 | 70.4 | 70.3 | 0.1 | 0.4 | 0.5 |
| ISTH 3 | 86 | 86.9 | 91.4 | 2.5 | 0.5 | 3.0 |
| CCNRP | 82 to 103 | 89.0 | 74.6 | 8.8 | 4.1 | 4.7 |
| Cntrl 3 | 65 | 64.4 | 52.1 | 10.5 | 0.5 | 11.0 |
| Cntrl 4 | 24.6 | 26.7 | 22.7 | 8.0 | 4.0 | 4.1 |
| JS | 0 | 0 | 0 | 0 | 0 | 0 |
| XX-01 | 200 | 136.4 | 119.5 | 6.6 | 18.9 | 25.2 |

ISTH = reference sample

As shown below in Table 3, the FACS assay resulted in VWF measurements comparable to a method used in clinical laboratories. Samples were normal individuals and individuals having VWD. Table 4 is similar to Table 3, except that the samples were from normal individuals and individuals having Type 2 VWD. Table 5 is also similar to Table 3, except that the samples were from individuals having Type 2M VWD.

TABLE 3

Summary of VWF:IbCo by FACS in Plasma Samples from African Americans and Caucasians with and without VWF Single Nucleotide Polymorphisms (SNPs).

| Sample | VWF:Ag 1 | VWF:RCo | Ratio 1 | VWF:Ag 2 | VWF:IbCo | Ratio 2 | Ratio 2/ Ratio 1 |
|---|---|---|---|---|---|---|---|
| IN-09 | 215 | 104 | 0.484 | 167 | 131 | 0.781 | 0.608 |
| XX-22 | 193 | 140 | 0.725 | 152 | 240 | 1.579 | 1.244 |
| XX-24 | 278 | 225 | 0.809 | 233 | 240 | 1.029 | 0.863 |
| XX-27 | 195 | 130 | 0.667 | 186 | 147 | 0.788 | 0.753 |
| XX-29 | 85 | 74 | 0.871 | 79 | 104 | 1.313 | 1.222 |
| AT-09 | 103 | 69 | 0.670 | 88 | 78 | 0.886 | 0.756 |
| AT-13 | 71 | 72 | 1.014 | 72 | 89 | 1.226 | 1.251 |
| AT-14 | 257 | 248 | 0.965 | 231 | 233 | 1.009 | 0.906 |
| AT-17 | 225 | 95 | 0.422 | 188 | 144 | 0.768 | 0.641 |
| AT-18 | 225 | 195 | 0.867 | 186 | 155 | 0.834 | 0.689 |
| XX-21 | 85 | 92 | 1.082 | 90 | 72 | 0.801 | 0.844 |
| AT-06 | 154 | 176 | 1.143 | 150 | — | — | — |
| IN-15 | 122 | 85 | 0.697 | 83 | 140 | 1.685 | 1.146 |
| PB-06 | 86 | 88 | 1.023 | 78 | 137 | 1.755 | 1.594 |

TABLE 3-continued

Summary of VWF:IbCo by FACS in Plasma Samples from African Americans and Caucasians with and without VWF Single Nucleotide Polymorphisms (SNPs).

| | | | | | | | |
|---|---|---|---|---|---|---|---|
| PB-14 | 234 | 211 | 0.902 | 238 | 197 | 0.831 | 0.843 |
| PB-17 | 109 | 93 | 0.853 | 104 | 68 | 0.649 | 0.620 |
| AT-16 | 82 | 94 | 1.146 | 73 | 94 | 1.284 | 1.143 |
| AT-19 | 164 | 151 | 0.921 | 147 | 126 | 0.859 | 0.771 |
| AT-42 | 86 | 69 | 0.802 | 70 | 64 | 0.902 | 0.739 |
| NO-53 | 243 | 252 | 1.037 | 239 | 159 | 0.666 | 0.655 |
| DT-08 | 68 | 71 | 1.044 | 58 | 62 | 1.064 | 0.910 |
| DT-01 | 88 | 107 | 1.216 | 91 | 82 | 0.906 | 0.937 |
| DT-06 | 82 | 79 | 0.963 | 83 | 82 | 0.981 | 0.995 |
| XX-04 | 96 | 109 | 1.135 | 86 | 128 | 1.481 | 1.334 |
| XX-06 | 129 | 149 | 1.155 | 111 | 128 | 1.148 | 0.993 |
| XX-13 | 124 | 169 | 1.363 | 114 | 186 | 1.638 | 1.503 |
| IN-13 | 103 | 92 | 0.893 | 100 | 88 | 0.887 | 0.859 |
| IN-22 | 96 | 110 | 1.146 | 104 | 65 | 0.627 | 0.678 |
| PB-09 | 88 | 78 | 0.886 | 100 | 77 | 0.767 | 0.870 |
| XX-03 | 106 | 136 | 1.283 | 103 | 160 | 1.551 | 1.511 |
| XX-12 | 137 | 183 | 1.336 | 128 | 189 | 1.437 | 1.380 |
| XX-14 | 115 | 163 | 1.417 | 109 | — | — | — |
| XX-15 | 123 | 137 | 1.114 | 159 | 122 | 0.768 | 0.992 |
| IN-01 | 209 | 220 | 1.053 | 149 | — | — | — |
| IN-03 | 71 | 68 | 0.958 | 68 | 54 | 0.801 | 0.762 |
| IN-07 | 95 | 85 | 0.895 | 77 | 76 | 0.995 | 0.802 |
| PB-01 | 84 | 77 | 0.917 | 82 | 71 | 0.862 | 0.805 |
| PB-04 | 155 | 162 | 1.045 | 146 | 105 | 0.722 | 0.678 |
| PB-20 | 107 | 114 | 1.065 | 91 | 95 | 1.046 | 0.855 |
| NO-23 | — | — | — | 143 | <1.1 | — | — |

1 = DT method (a clinical laboratory method)

2 = BRI method (Blood Research Institute method)

Shaded area = <0.81

TABLE 4

VWF:IbCo by FACS in Plasma from African Americans and Caucasians With/Without Type 2 VWD and Repeats.

| Sample | Race | VWD Phenotype | VWF Mutation | VWF:Ag | VWF:RCo | RCo/Ag | FACS1 | FACS1/Ag | FACS2 | FACS2/Ag |
|---|---|---|---|---|---|---|---|---|---|---|
| DB | AA | “2M” | 3 AA snps | 86 | 47 | 0.547 | 78 | 0.910 | 78 | 0.905 |
| MK0055 | AA | “2M” | P1467S | 257 | 36 | 0.140 | 214 | 0.833 | 184 | 0.718 |
| LJ | C | “2M” | 3 AA snps | 66 | 40 | 0.606 | 180 | 2.734 | 48 | 0.735 |
| IN0061 | | 2M | R1374C | 22 | 11 | 0.500 | 4 | 0.204 | 10 | 0.432 |
| RH | | 2B | R1308S | 43 | 37 | 0.860 | 67 | 1.558 | 67 | 1.557 |
| LB | | 2B | V1316M | 91 | 62 | 0.681 | 159 | 1.751 | 106 | 1.162 |
| SB | | 2B | V1316M | 27 | 12 | 0.444 | 36 | 1.347 | 25 | 0.914 |
| AJ | | 2B | H1268D | 21 | 17 | 0.810 | 31 | 1.484 | 41 | 1.959 |
| PB0068 | | 2B | R1306W | 23 | 13 | 0.565 | — | — | 25 | 1.065 |
| YG | | 2A | L1503P | 26 | 13 | 0.500 | — | — | 19 | 0.714 |
| AV | | 2A | G1579R | 46 | 16 | 0.348 | — | — | 1 | 0.028 |
| AT0021 | | 2A | M7401? | 31 | 12 | 0.387 | — | — | 18 | 0.574 |
| AT0032 | | 2A | I1628T | 120 | 32 | 0.267 | — | — | 103 | 0.586 |
| IA0001 | | 2A | R1597W | 33 | <10 | — | — | — | 8 | 0.247 |
| AT0017 | AA | NL | 3 AA snps | 225 | 95 | 0.422 | 144 | 0.641 | 156 | 0.695 |
| XX0027 | AA | NL | 3 AA snps | 195 | 130 | 0.677 | 147 | 0.753 | 116 | 0.595 |
| XX0004 | C | NL | — | 96 | 109 | 1.135 | 128 | 1.334 | 114 | 1.183 |

TABLE 4-continued

VWF:IbCo by FACS in Plasma from African Americans and Caucasians With/Without Type 2 VWD and Repeats.

| Sample | Race | VWD Phenotype | VWF Mutation | VWF:Ag | VWF:RCo | RCo/Ag | FACS1 | FACS1/Ag | FACS2 | FACS2/Ag |
|---|---|---|---|---|---|---|---|---|---|---|
| XX0013 | C | NL | — | 124 | 169 | 1.363 | 186 | 1.503 | 105 | 0.843 |
| PB0014 | AA | NL | — | 234 | 211 | 0.902 | 197 | 0.843 | 213 | 0.909 |
| AT0042 | AA | NL | — | 86 | 69 | 0.802 | 64 | 0.739 | 91 | 1.056 |

AA = African American
C = Caucasian
NL = normal
"2M" = apparent type 2M

TABLE 5

VWF Function in Plasma from African Americans and Caucasians With/Without Type 2M VWD.

| Sample | Race | VWD Phenotype | VWF Mutation | VWF:Ag 1 | VWF:RCo 1 | RCo/Ag 1 | FACS2 | FACS2/Ag |
|---|---|---|---|---|---|---|---|---|
| TB | C | "2M" | — | 127 | 87 | 0.69 | 87 | 0.69 |
| DB | AA | "2M" | 3 AA snps | 86 | 47 | 0.55 | 78 | 0.91 |
| AC | C | 2M | G13242S | 95 | 13 | 0.14 | <1.1 | — |
| BF | — | 2M | I1416T (new) | 89 | 31 | 0.35 | 36 | 0.41 |
| MG | H | 2M | I1425F | 45 | 16 | 0.36 | >1.1 | — |
| LG | C | 2M | E1359K | 67 | 37 | 0.55 | 27 | 0.41 |
| GI | — | 2M | D1283H (new) | 16 | 4 | 0.25 | <1.1 | — |
| KJ | C | 2M | — | 12 | 3 | 0.25 | <1.1 | — |
| LJ | AA | "2M" | 3 AA snps | 66 | 40 | 0.61 | 180 | 2.73 |
| BM | C | 2M | I1426T | 156 | 43 | 0.28 | 93 | 0.60 |
| AR | — | 2M | R1374L | 48 | 10 | 0.21 | <1.1 | — |
| DR | AA | "2M" | R1342C; I1343V; 1301-3103 del; and R2185Q | 38 | 12 | 0.32 | 37 | 0.97 |
| MK0038 | C | 2M | R1392-Q1402 del | 47 | 11 | 0.23 | <1.1 | — |
| IN0061 | C | 2M | R1374C | 22 | 11 | 0.50 | 4 | 0.20 |
| MK0055 | AA | "2M" | P1467S | 257 | 36 | 0.14 | 214 | 0.83 |
| MK0058 | AA | "2M" | P1467S | 265 | 68 | 0.14 | 194 | 0.73 |

AA = African American
C = Caucasian
H = Hispanic

Figure 4:
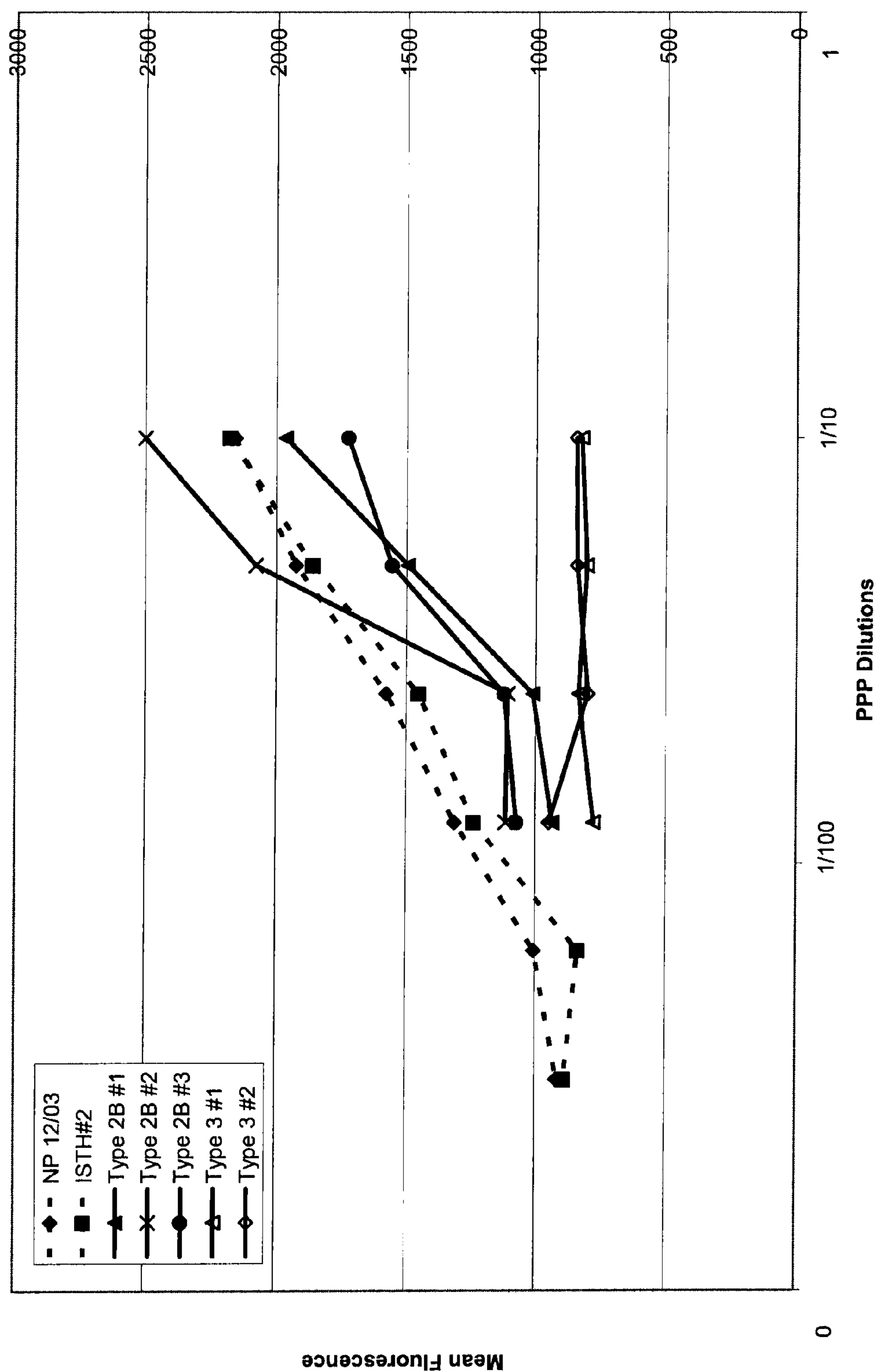
FIG. 4 shows an FACS assay with additional samples from individuals having type 2B VWD, which has gain-of-function VWF mutations (y-axis is mean fluorescence and x-axis is platelet poor plasma (PPP) dilutions).

Results: As shown in FIG. 4, individuals with normal VWF showed a typical increase in mean fluorescence with lower dilutions of their plasma. As expected, individuals with Type 3 VWD showed change in mean fluorescence because their plasma has low or no VWF.

Figure 5:
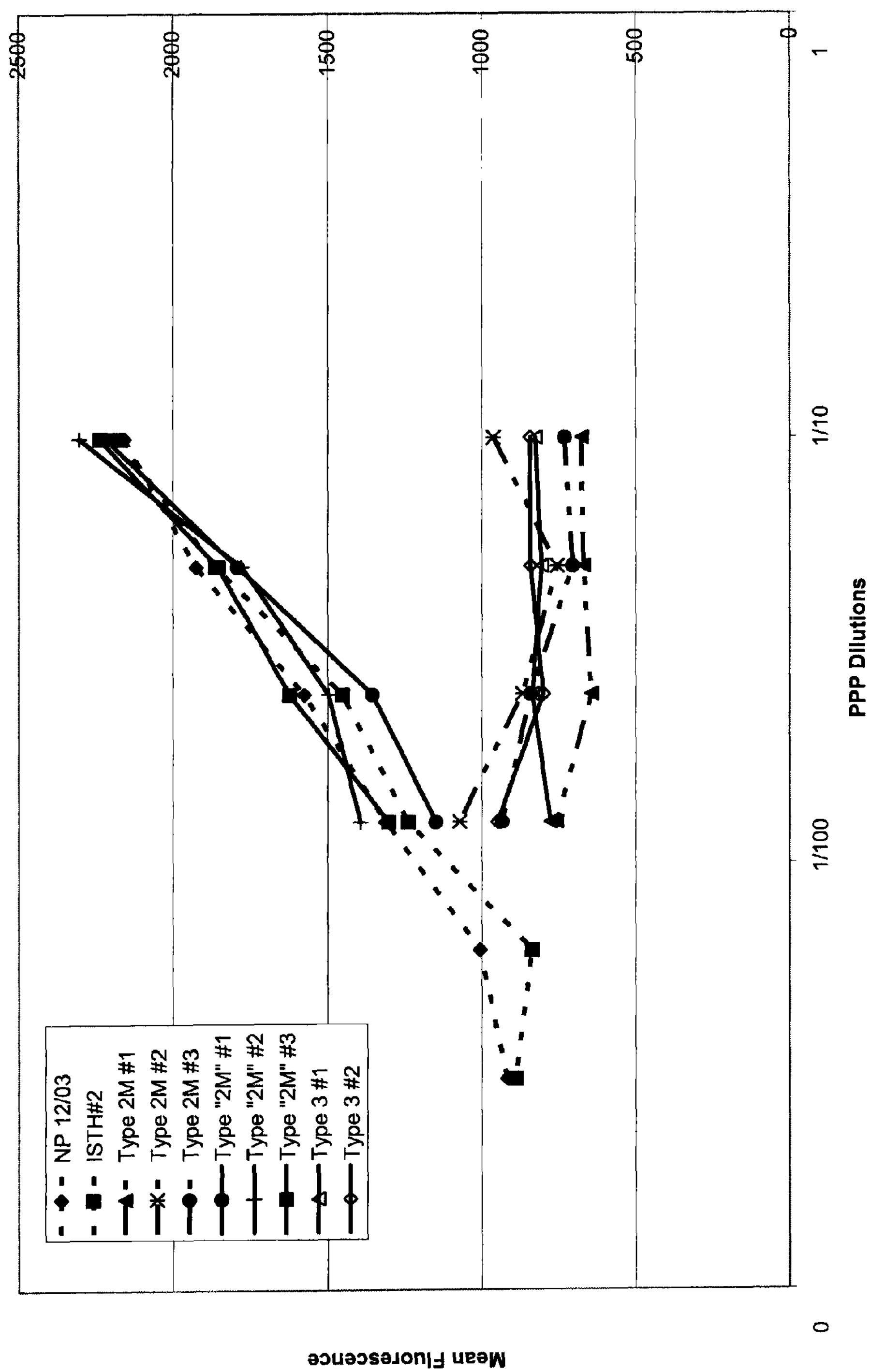
FIG. 5 shows a FACS assay with additional samples from individuals having type 2M VWD, which has low GPIb binding, and apparent type 2M VWD, which has low VWF:RCo/VWF:Ag, yet normal levels of VWF (y-axis is mean fluorescence and x-axis is platelet poor plasma (PPP) dilutions).

As shown in FIG. 5, individuals with Type 2B VWD showed a much earlier increase in mean fluorescence when compared to normals, starting at very high dilutions of their plasma (i.e., >1/100). Type 2B VWD is characterized as having gain-of-function mutations. Again, individuals with Type 3 VWD showed no reaction in the assay.

Figure 6:
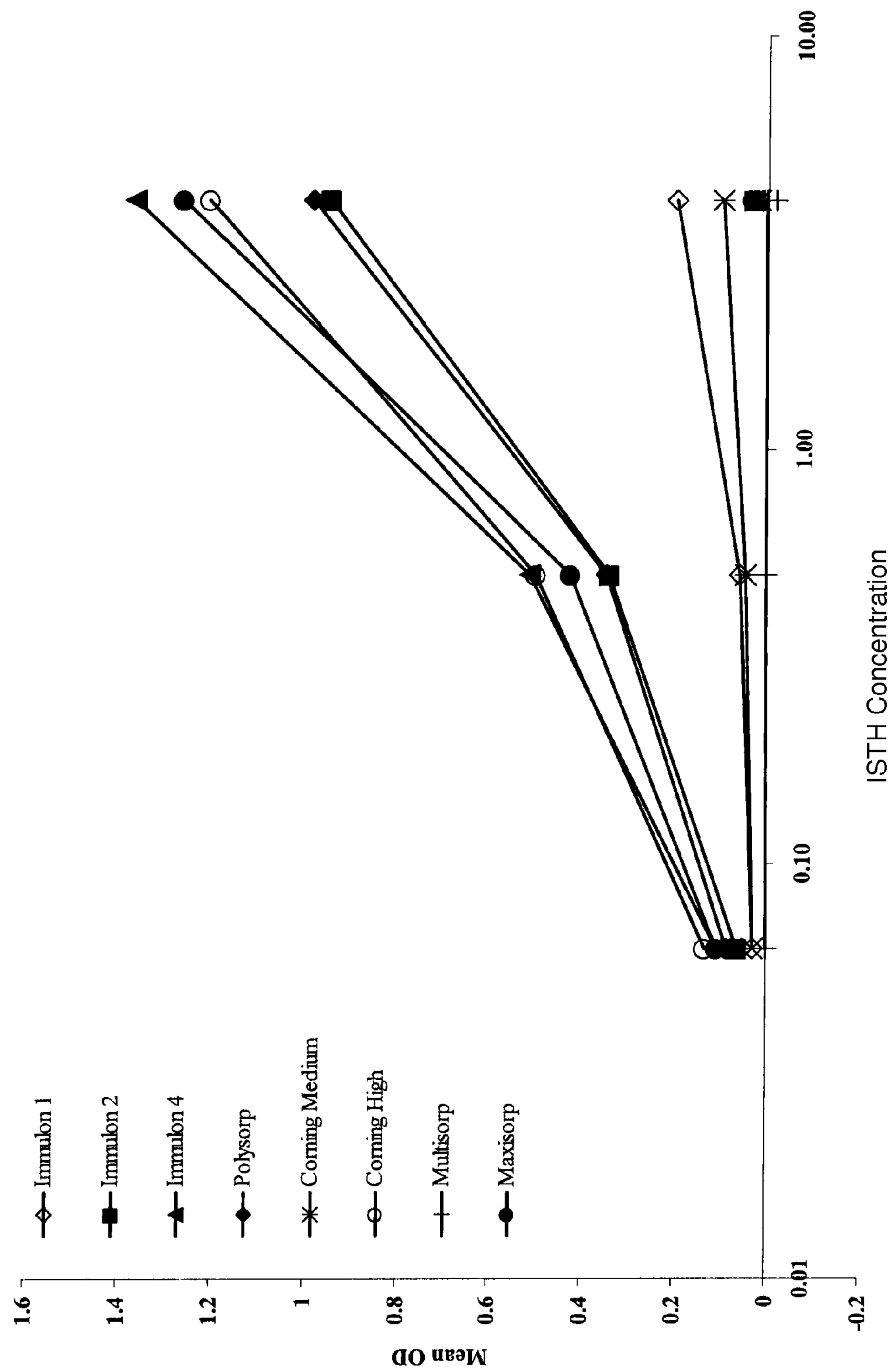
FIG. 6 shows the effect of charge on the solid-phase surface during an ELISA with immobilized GPIbα having two platelet-type, pseudo VWD mutations (y-axis is mean fluorescence and x-axis is ISTH (a standard) concentration in U/dL).

As shown in FIG. 6, individuals with Type 2M VWD showed no increase in mean fluorescence when compared to normals. Type 2M VWD is characterized by defective VWF that does not interact with GPIbα. Individuals with apparent Type 2M ("2M") showed a much earlier increase in mean fluorescence when compared to normals, starting at very high dilutions of their plasma (i.e., >1/100). Apparent Type 2M is characterized by low VWF:RCoNWF:Ag, yet normal levels of VWF. Again, individuals with Type 3 VWD showed no reaction in the assay.

Example 3

Mutant GPIbα Function in ELISA

S2 cells (Invitrogen) were stably transfected with a mutant GPIbα construct, a wild-type GPIbα construct and a GP-IX construct. In some experiments, S2 cells were transfected with GPIbα constructs having a C65A mutation and ΔTM290 mutation. The C65A mutation removed a cysteine that could potential allow dimerization of GPIbα; and the ΔTM290 mutation removed the transmembrane region so that the expressed protein was excreted.

Briefly, the constructs were cloned into a pMT/Bip/V5-His:GPIbα C65A,D235Y,M239V ΔTM290 or pMT/Bip/V5-His:GPIbα C65A ΔTM290 secretion vector (Invitrogen). On day 1, S2 cells were counted and seeded into a 35 mm dish or a well of a 6 well plate at $3\times10^6$ cells in 3 ml of complete medium (Ex-Cell 420+10% FBS+7 mM L-Glutamine). The cells were allowed to grow 6-8 hours at 28° C. The following was added to one set of tubes: Solution A, which contained 36 μl of 2M $CaCl_2$, 19 μg of plasmid DNA (purified with Qiagen Maxi Kit; Qiagen; Valencia, Calif.), 1 μg pCoBlast (selection vector) and $ddH_2O$ up to 300 μl. The following was added to another set of tubes: Solution B, which contained 300 μl of 2× HEPES buffered saline. Solution A was slowly added dropwise to solution B while gently vortexing. The combined solutions then were incubated at room temperature for 30-40 minutes until a fine precipitate formed. The mixed solution was added dropwise to the plated cells while gently swirling the plate. The cells were then incubated overnight at 28° C. (about 16-24 hours).

The next day, the transfection solution was removed and replaced with 3 ml of fresh complete medium and incubated at 28° C. without $CO_2$. On day 5, the cells were resuspended cells and transferred to a 15 cc conical tube, centrifuged at 2400 rpm for 2 minutes. The medium was decanted, and the cells were resuspended in 3 ml of stable medium (complete medium+25 μg/ml Blastidin-S) and plated in a new dish or well.

Selection began on week 2. As done on Day 5, the selection medium was replaced every 3-4 days with 3 ml fresh selection medium. Selection and expansion continued through week 3. During this time, the cells were resuspended, transferred to 15 cc conical tubes, and centrifuged at 2400 rpm for 2 minutes. The media as decanted, and the cells were resuspended in 5 ml of selector media and plated in new T25 flask. After 4 days, the cells were expanded from 1 T25 to 2 T25 flasks.

Expansion and freezing stocks began on week 4. Cells were expanded from the T25 flasks to T75 flasks ($3\times10^6$ cells/ml medium). T75 flasks received 15 ml medium, which was about $45\times10^6$ cells. The remaining cells (about $2\times10^7$ cells/vial) were frozen and stored in liquid nitrogen.

Induction of the cells in the T75 flasks began on week 5. Cells were resuspended, transferred to a 15 cc conical tube for counting and centrifuged. $45\times10^6$ cells were resuspended 15 ml induction medium (stable medium+500 μM $CuSO_4$) and transferred to T75 flasks. The cells were then incubated 4 days at 28° C., the supernatant having secreted GPIbα was harvested.

Figure 3:
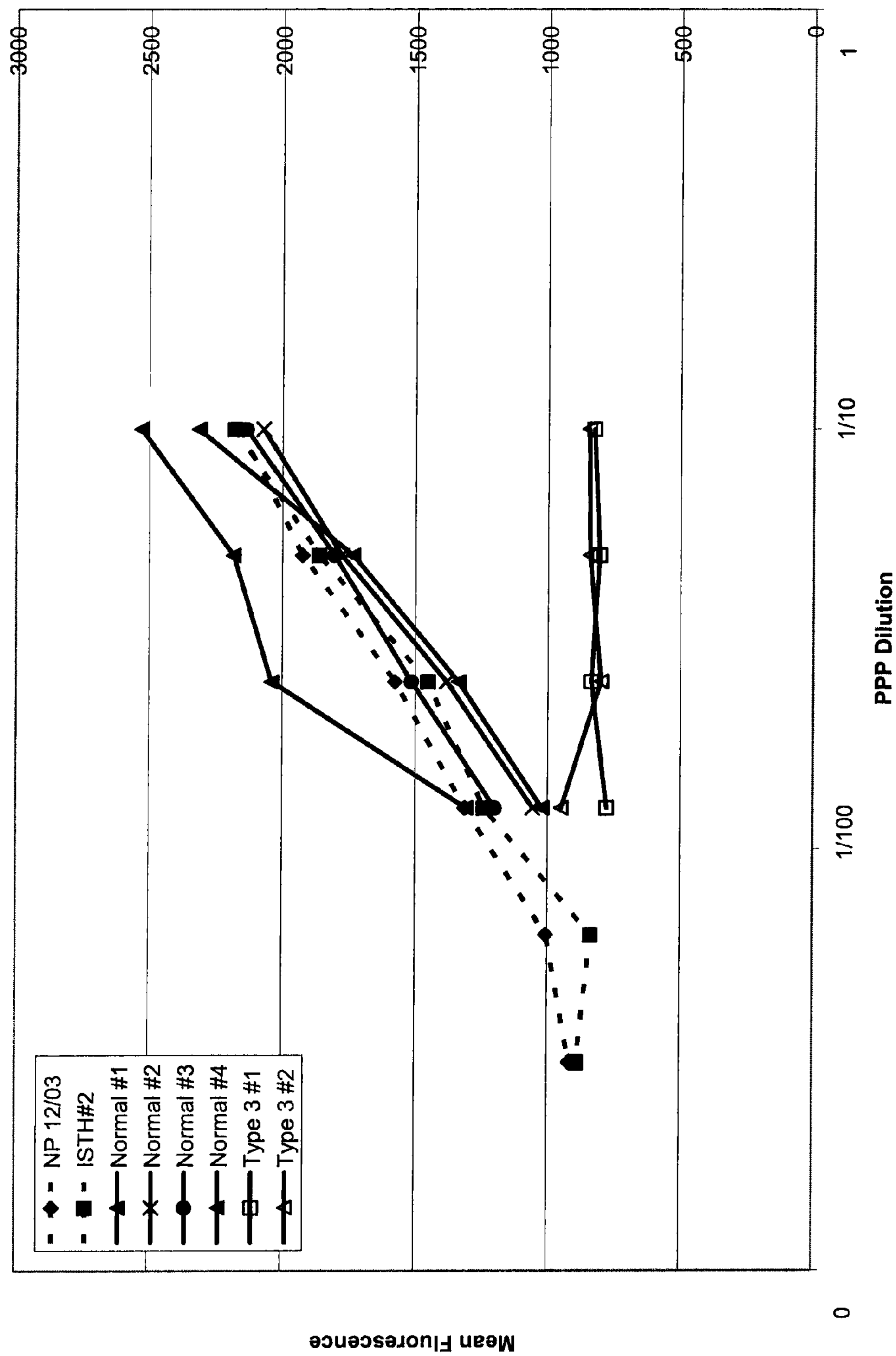
FIG. 3 shows an FACS assay with GPIbα having two platelet-type, pseudo VWD mutations using samples from control individuals and with type 3 VWD, which has low to undetectable VWF (y-axis is mean fluorescence and x-axis is platelet poor plasma (PPP) dilutions).

As shown Table 6 and FIG. 3, various solid-phase surfaces were first tested for the ELISA assays. Table 6 shows that the surface density of GPIbα was affected by the surface charge of the solid-phase surface; whereas FIG. 3 shows that different solid-phase surfaces coated with GPIbα having a double mutation affected VWF binding. Solid-phase surface charge appeared to affect GPIbα/VWF binding, suggesting that any solid-phase surface should first be tested for it ability (1) to provide a uniform density of GPIbα and (2) to permit VWF to bind to the GPIbα. After considering both Table 6, and FIG. 3, Immulon® 4 HBX Plates worked best and were used thereafter.

TABLE 6

Effect of Various Solid-Phase Surfaces on Concentration of GPIbα Double Mutation (G233V/M239V) (same samples on different plates).

| Solid-Phase Surface | Characteristic of the Surface | Calculated concentration GPIbα |
|---|---|---|
| Immulon 1 | Hydrophobic | 635.1 |
| Immulon 2 | Hydrophobic | 370.8 |
| Immulon 4 | Maximum | 383.7 |
| Polysorp | Hydrophobic | 321.7 |
| Corning Medium | Hydrophobic | 576.8 |
| Corning High | Ionic and/or Hydrophobic | 414.7 |
| Multisorb | Polar Molecules | No binding |
| Maxisorb | Hydrophobic/Hydrophilic | 408.5 |

An Immulon 4 HBX Plate (Thermo Scientific; Waltham, Mass.) was coated with anti-GPIbα monoclonal antibody 142.16 (Blood Research Institute) at a concentration of 5 μg/ml, which was then incubated overnight at 4° C. The plate was blocked with PBS containing 1% BSA for 1 hour at room temperature. Nickel-purified S2-expressed proteins—GPIbα C65A, D235Y, M239V and ΔTM290—were diluted in PBS containing 1% BSA and incubated on the anti-GPIbα antibody-coated plate for 1 hour at 37° C. See, Celikel et al., supra.

PPP from controls or individuals having VWD was diluted 1:50 in PBS containing 1% BSA and serially diluted 1:2 to a final dilution of 1:100. Diluted PPP was added to the plate and incubated for 1 hour at 37° C. ISTH Lot#3 was again used as a standard, with curve dilutions starting at 1:25 in substrate buffer, which was then serially diluted 1:2 to a final dilution of 1:1600. 2 μg/ml biotinylated AVW-1 and AVW-15 (Blood Research Institute) were added to the plate and incubated for 30 minutes at 37° C. Finally, streptavidin-conjugated alkaline phosphatase (Jackson ImmunoResearch Laboratories, Ltd.; West Grove, Pa.), diluted 1:5000 in substrate buffer, was added to the plate and incubated for 30 minutes at 37° C. p-Nitrophenyl Phosphate (PNPP; Invitrogen), an alkaline phosphate substrate, was diluted 1:100 in substrate buffer and added to the plate. The plate was read at 405/650 nm on a plate reader. The plate was washed three times between each step with PBS containing 0.05% Tween-20.

Results: As shown in Tables 7 and 8, individuals with normal VWF showed similar ELISA results whether ristocetin was added to the assay or not. In addition, the ELISA assay resulted in VWF measurements comparable to a method used in clinical laboratories

TABLE 7

Summary of VWF:IbCo by ELISA in Plasma Samples from African Americans and Caucasians with and without VWF Single Nucleotide Polymorphisms (SNPs).

| Subject | VWF:Ag | IbCo ELISA | Ristocetin ELISA | IbCo/VWF:Ag | Ris/VWF:Ag | Clinical VWF:Ag | VWF:RCo | VWF:RCo/ VWF:Ag |
|---|---|---|---|---|---|---|---|---|
| ISTH 3 A | 121.25 | 109.4 | 127.3 | 0.90 | 1.05 | 106 | 86 | 0.81 |
| ctrl 5 (70%) | 75.62 | 68.97 | 69.68 | 0.91 | 0.92 | 74.2 | 60.2 | 0.81 |
| ctrl 6 (35%) | 32.28 | 31.12 | 28.76 | 0.96 | 0.89 | 37.1 | 30.1 | 0.81 |
| CCNRP 7122 A | 94.56 | 84.6 | 73.34 | 0.89 | 0.78 | 114 | 71 | 0.62 |
| ISTH 3 B | 96.71 | 99.71 | 104.05 | 1.03 | 1.08 | 106 | 86 | 0.81 |
| MK0038 | 33.44 | 1.41 | 14.16 | 0.04 | 0.42 | 47 | 11 | 0.23 |
| XX0017 | 139.5 | 157.35 | 169.5 | 1.13 | 1.22 | 206 | 200 | 0.97 |
| JS | 0 | 0.5 | 0.99 | 0.00 | 0.00 | <1 | <10 | 0.00 |

TABLE 7-continued

Summary of VWF:IbCo by ELISA in Plasma Samples from African Americans and Caucasians with and without VWF Single Nucleotide Polymorphisms (SNPs).

| Subject | VWF:Ag | IbCo ELISA | Ristocetin ELISA | IbCo/VWF:Ag | Ris/VWF:Ag | Clinical VWF:Ag | VWF:RCo | VWF:RCo/ VWF:Ag |
|---|---|---|---|---|---|---|---|---|
| ctrl 8 (30%) | 23.84 | 26.96 | 23.58 | 1.13 | 0.99 | 31.8 | 25.8 | 0.81 |
| ISTH 3 C | 85.14 | 94.42 | 90.48 | 1.11 | 1.06 | 106 | 86 | 0.81 |
| CCNRP 7122 B | 59.61 | 60.64 | 55.44 | 1.02 | 0.93 | 114 | 71 | 0.62 |
| AT0068 | 70.4 | 59.18 | 31.47 | 0.84 | 0.45 | 99 | 57 | 0.58 |

TABLE 8

Summary of VWF:IbCo by ELISA in Plasma Samples from African Americans and Caucasians with and without VWF Single Nucleotide Polymorphisms (SNPs).

| Subject | Clinical VWF:Ag | BRI VWF:Ag | Clinical VWF:RCo | IbCo ELISA | Ristocetin ELISA | Clinical VWF:RCo/ VWF:Ag | IbCo ELISA/BRI VWF:Ag |
|---|---|---|---|---|---|---|---|
| AA w/1380 + 1435 + 1472 | | | | | | | |
| HN | 334 | 228 | 165 | 165 | — | 0.494 | 0.725 |
| XX | 278 | 228 | 225 | 235 | 222 | 0.809 | 1.029 |
| AT | 257 | 309 | 248 | 234 | 220 | 0.965 | 0.759 |
| AT | 225 | 159 | 198 | 149 | 152 | 0.880 | 0.932 |
| AT | 225 | 172 | 95 | 67 | 106 | 0.422 | 0.393 |
| IN | 215 | 179 | 104 | 77 | 73 | 0.484 | 0.429 |
| XX | 193 | 200 | 140 | 123 | 154 | 0.725 | 0.616 |
| NO | 179 | 178 | 180 | 171 | — | 1.006 | 0.960 |
| AT | 103 | 83 | 69 | 58 | 64 | 0.670 | 0.701 |
| XX | 85 | 67 | 74 | 73 | 57 | 0.871 | 1.095 |
| AT | 71 | 65 | 72 | 70 | 53 | 1.014 | 1.077 |
| HN | 67 | 77 | 54 | 54 | — | 0.806 | 0.704 |
| AA w/1472 alone | | | | | | | |
| NO | 259 | 209 | 224 | 151 | 213 | 0.865 | 0.723 |
| XX | 195 | 129 | 130 | 118 | 132 | 0.667 | 0.910 |
| XX | 185 | 143 | 154 | 143 | 183 | 0.832 | 1.001 |
| XX | 167 | 172 | 170 | 123 | 198 | 1.018 | 0.714 |
| NO | 166 | 151 | 175 | 155 | — | 1.054 | 1.025 |
| IN | 153 | 123 | 146 | 120 | 55 | 0.954 | 0.970 |
| NO | 144 | 141 | 85 | 92 | — | 0.590 | 0.652 |
| DT | 141 | — | 121 | — | — | 0.858 | — |
| HN | 139 | — | 98 | — | — | 0.705 | — |
| XX | 137 | 112 | 123 | 90 | 151 | 0.898 | 0.801 |
| HN | 136 | 136 | 113 | 106 | — | 0.831 | 0.784 |
| XX | 122 | 89 | 85 | 75 | — | 0.697 | 0.839 |
| XX | 116 | 103 | 89 | 82 | 81 | 0.767 | 0.793 |
| XX | 110 | 104 | 91 | 100 | 62 | 0.827 | 0.967 |
| IN | 108 | 107 | 101 | 86 | 94 | 0.935 | 0.800 |
| AT | 99 | 91 | 57 | 50 | 25 | 0.576 | 0.550 |
| DT | 98 | 89 | 85 | 79 | 85 | 0.867 | 0.885 |
| AT | 84 | 96 | 79 | 82 | 63 | 0.940 | 0.856 |
| AA w/no SNPs | | | | | | | |
| NO | 243 | 237 | 252 | 217 | — | 1.037 | 0.917 |
| PB | 234 | 192 | 211 | 110 | 83 | 0.902 | 0.576 |
| DT | 224 | 185 | 167 | 190 | — | 0.746 | 1.025 |
| AT | 199 | 178 | 193 | 177 | — | 0.970 | 0.993 |
| NO | 195 | 179 | 220 | 207 | 233 | 1.128 | 1.160 |
| AT | 164 | 132 | 151 | 98 | 96 | 0.921 | 0.743 |
| AT | 154 | 139 | 176 | 159 | 135 | 1.143 | 1.143 |
| IN | 122 | 76 | 85 | 68 | 74 | 0.697 | 0.897 |
| PB | 109 | 91 | 93 | 76 | 63 | 0.853 | 0.832 |
| PB | 86 | 63 | 88 | 64 | 52 | 1.023 | 1.025 |
| AT | 86 | 107 | 97 | 68 | 63 | 1.128 | 0.633 |

TABLE 8-continued

Summary of VWF:IbCo by ELISA in Plasma Samples from African Americans and Caucasians with and without VWF Single Nucleotide Polymorphisms (SNPs).

| Subject | Clinical VWF:Ag | BRI VWF:Ag | Clinical VWF:RCo | IbCo ELISA | Ristocetin ELISA | Clinical VWF:RCo/ VWF:Ag | IbCo ELISA/BRI VWF:Ag |
|---|---|---|---|---|---|---|---|
| AT | 86 | 57 | 69 | 60 | 56 | 0.802 | 1.055 |
| XX | 85 | 79 | 92 | 65 | 44 | 1.082 | 0.817 |
| AT | 82 | 93 | 94 | 70 | 49 | 1.146 | 0.750 |
| C w/1380 + 1435 + 1472 | | | | | | | |
| PB | 180 | 144 | 149 | 122 | 115 | 0.828 | 0.842 |
| IN | 94 | 91 | 84 | 68 | 79 | 0.894 | 0.747 |
| C w/1472 alone | | | | | | | |
| XX | 206 | 254 | 200 | 266 | 251 | 0.971 | 1.050 |
| IN | 192 | 137 | 144 | 133 | 126 | 0.750 | 0.973 |
| DT | 174 | 148 | 137 | 165 | 127 | 0.787 | 1.119 |
| IN | 171 | 106 | 122 | 94 | 127 | 0.713 | 0.888 |
| PB | 129 | 102 | 85 | 76 | 66 | 0.659 | 0.751 |
| IN | 111 | 88 | 99 | 76 | 78 | 0.892 | 0.861 |
| XX | 97 | 67 | 89 | 82 | 80 | 0.918 | 1.224 |
| HN | 94 | 103 | 82 | 82 | — | 0.872 | 0.791 |
| IN | 91 | 65 | 88 | 58 | 51 | 0.967 | 0.902 |
| C w/no SNPs | | | | | | | |
| PB | 289 | 313 | 256 | 309 | 292 | 0.886 | 0.988 |
| IN | 237 | 171 | 255 | 154 | 275 | 1.076 | 0.901 |
| IN | 187 | 165 | 138 | 124 | 144 | 0.738 | 0.753 |
| XX | 129 | 121 | 149 | 90 | 112 | 1.155 | 0.745 |
| XX | 124 | 128 | 169 | 137 | 127 | 1.363 | 1.073 |
| IN | 103 | 82 | 92 | 67 | 78 | 0.893 | 0.815 |
| IN | 100 | 71 | 91 | 68 | 72 | 0.910 | 0.957 |
| XX | 96 | 93 | 109 | 132 | 103 | 1.135 | 1.425 |
| IN | 96 | 86 | 110 | 94 | 87 | 1.146 | 1.086 |
| XX | 94 | 77 | 101 | 74 | 83 | 1.074 | 0.972 |
| XX | 94 | 100 | 86 | 88 | 93 | 0.915 | 0.875 |
| DT | 88 | 90 | 107 | 91 | 83 | 1.216 | 1.008 |
| PB | 88 | 79 | 78 | 50 | 54 | 0.886 | 0.628 |
| IN | 85 | 61 | 77 | 58 | 57 | 0.906 | 0.961 |
| IN | 85 | 74 | 82 | 65 | 56 | 0.965 | 0.872 |
| PB | 83 | 80 | 88 | 60 | 51 | 1.060 | 0.742 |
| DT | 82 | 73 | 79 | 65 | 63 | 0.963 | 0.891 |
| PB | 74 | 52 | 69 | 53 | 34 | 0.932 | 1.017 |
| DT | 68 | 57 | 71 | 55 | 56 | 1.044 | 0.956 |
| XX | 58 | 54 | 61 | 52 | 49 | 1.052 | 0.958 |

AA = African American
C = Caucasian

Thus, measurement of VWF function using a VWF:IbCo FACS or ELISA assay more directly correlates with VWF function and avoids some of the pitfalls and functional variability observed with VWF:RCo assays.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method of measuring von Willebrand factor (VWF) without using a platelet agglutination agonist, the method comprising the steps of:

providing a solid phase surface comprising immobilized platelet glycoprotein Ibα(GPIbα) or a functional fragment thereof, wherein the solid phase surface is latex and wherein the immobilized GPIbα or functional fragment thereof comprises at least two mutations selected from the group consisting of G233V, D235Y and M239V relative to SEQ ID NO:2, wherein one of the mutations is D235Y;

contacting a sample having or suspected of having VWF with the surface, wherein the contacting is done without a platelet aggregation agonist; and detecting a complex of VWF and GPIbα.

2. The method of claim 1, wherein the solid-phase surface comprises an anti-GPIbα antibody that binds the GPIbα or functional fragment thereof.

3. The method of claim 1, wherein the sample is plasma.

4. The method of claim 1, wherein the at least two mutations are selected from the group consisting of D235Y/G233V, and D235Y/M239V.

5. The method of claim 1, wherein the at least two mutations are D235Y/G233V/M239V.

6. The method of claim 1, wherein a labeled anti-VWF antibody is used to detect the complex of VWF and GPIbα.

7. A kit for measuring active von Willebrand factor (VWF), the kit comprising:

recombinant platelet glycoprotein Ibα (GPIbα) or a functional fragment thereof, wherein the GPIbα or functional fragment thereof comprises at least two mutations selected from the group consisting of G233V, D235Y and M239V relative to SEQ ID NO:2, wherein one of the mutations is D235Y; and a reagent to detect a complex of VWF and GPIbα.

8. The kit of claim 7, wherein the reagent is a labeled anti-VWF antibody.

9. The kit of claim 7, further comprising a control, wherein the control is a plasma sample from an individual that does not have von Willebrand disease (VWD).

10. The kit of claim 7, wherein the GPIbα or functional fragment thereof having the at least two mutations selected from the group consisting of G233V, D235Y and M239V relative to SEQ ID NO:2 is immobilized on a surface.

11. The kit of claim 10, wherein the surface is a host cell surface, and wherein the host cell does not natively express GPIbα.

12. The kit of claim 11, wherein the host cell for the host cell surface is selected from the group consisting of a *Xenopus* oocyte, a CHO-K1 cell, a L929 cell, a HEK-293T cell, a COS-7 cell and a S2 cell, and wherein the host cell is engineered to comprise a polynucleotide encoding GPIbα or functional fragment thereof having the at least two mutations selected from the group consisting of G233V, D235Y and M239V relative to SEQ ID NO:2, wherein one of the mutations is D235Y.

13. The kit of claim 11, wherein the host cell surface also comprises glycoprotein Ibβ (GPIbβ) and optionally glycoprotein IX (GP-IX), wherein GPIbβ comprises SEQ ID NO:4 and GP-IX comprises SEQ ID NO:8.

14. The kit of claim 10, wherein the surface is a solid-phase surface selected from the group consisting of agarose, glass, latex and plastic.

15. The kit of claim 14, wherein the solid-phase surface comprises an anti-GPIbα antibody that binds to GPIbα or functional fragment thereof.

16. The kit of claim 7, wherein the at least two mutations are selected from the group consisting of D235Y/G233V, D235Y/M239V, and D235Y/G233V/M239V.

* * * * *